United States Patent
Davis

(10) Patent No.: US 8,093,297 B2
(45) Date of Patent: *Jan. 10, 2012

(54) METHODS FOR CONCOMITANT ADMINISTRATION OF COLCHICINE AND A SECOND ACTIVE AGENT

(75) Inventor: Matthew W. Davis, Erwinna, PA (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/092,459

(22) Filed: Apr. 22, 2011

(65) Prior Publication Data

US 2011/0190397 A1 Aug. 4, 2011

Related U.S. Application Data

(63) Continuation of application No. 12/909,171, filed on Oct. 21, 2010, which is a continuation of application No. 12/372,046, filed on Feb. 17, 2009, now Pat. No. 7,820,681.

(60) Provisional application No. 61/138,141, filed on Jan. 14, 2009, provisional application No. 61/152,067, filed on Feb. 12, 2009.

(51) Int. Cl.
| | |
|---|---|
| A01N 37/18 | (2006.01) |
| A61K 31/16 | (2006.01) |
| C07C 233/00 | (2006.01) |
| C07C 235/00 | (2006.01) |
| C07C 237/00 | (2006.01) |
| C07C 239/00 | (2006.01) |
| C07C 211/00 | (2006.01) |
| C07C 205/00 | (2006.01) |
| C07C 207/00 | (2006.01) |

(52) U.S. Cl. ........ 514/629; 564/123; 564/308; 564/427; 568/306

(58) Field of Classification Search .................. 514/629; 564/123, 308, 427; 568/306
See application file for complete search history.

(56) References Cited

U.S. PATENT DOCUMENTS

| | | | |
|---|---|---|---|
| 5,426,224 A | 6/1995 | Lee et al. | |
| 5,914,332 A | 6/1999 | Sham et al. | |
| 5,968,972 A | 10/1999 | Broder et al. | |
| 6,037,157 A | 3/2000 | Norbeck et al. | |
| 6,245,805 B1 | 6/2001 | Broder et al. | |
| 6,896,900 B2 | 5/2005 | Gosselin et al. | |
| 7,601,758 B1 | 10/2009 | Davis | |
| 7,619,004 B1 | 11/2009 | Davis | |
| 7,820,681 B1 | 10/2010 | Davis | |
| 7,906,519 B2 | 3/2011 | Davis | |
| 7,915,269 B2 | 3/2011 | Davis | |
| 7,935,731 B2 * | 5/2011 | Davis | 514/630 |

OTHER PUBLICATIONS

U.S. Appl. No. 12/687,406, filed Jan. 2010, Davis.*
U.S. Appl. No. 12/407,980, filed Mar. 2009, Davis.*
U.S. Appl. No. 12/576,355, filed Oct. 2009, Davis.*
U.S. Appl. No. 12/909,171, filed Oct. 2010, Davis.*
U.S. Appl. No. 12/545,120, filed Aug. 2009, Davis.*
U.S. Appl. No. 13/090,697, filed Apr. 2011, Davis.*
U.S. Appl. No. 13/109,034, filed May 2011, Davis.*
U.S. Appl. No. 13/110,087, filed May 2011, Davis.*
Wang et al. 2001, "HMG-CoA reductase inhibitors (Statins) characterized as direct inhibitors of P-glycoprotein." Pharmaceutical Research, vol. 18, No. 6, pp. 800-806.*
Heeswijk et al. "Once-daily Dosing of Saquinavir and Low-dose Ritonavit in HIV-1-infected Individuals: a Pharmacokinetic Pilot Study"; ADS; 14; pp. F103-F110; (2000).
Creighton, et al.; "Is Ritonavir Boosting Associated With Gout?"; International Journal of ST & AIDS; 16: 362-364; (2005).
Drugs.Com; "Colchicine and Ritonavir Interactions"; printed Jan. 5, 2009; "colchicine"; printed Jan. 9, 2009; and "ritonavir", printed Jan. 9, 2009.
Zhou, et al; •Clinical Outcomes and Management of Mechanism-Based Inhibition of Cytochrome P450 3A4•; Therapeutics and Clinical Risk Management; 1; pp. 3-13; (2005).
Horn Et Al; •Life-Threatening Colchicine Drug Interactions; Pharmacy Times; P. 111; (May 2006).
Hsu, et al; "Ritonavir; Clinical Pharmacokinetics and Interactions with Other Anti-HIV Agents"; Clinical Pharmacokinet; 35; pp. 275-291; (1998).
Lacy et al. (Lexi-Comp's Clinical Reference Library, Drug Information Handbook, 7th Ed., 1999-2000, pp. 108-9 and 292-3.
Leiken et al., "Colchicine"; Poisoning and Toxicology Handbook (4th Ed.), Aug. 2007, p. 216.
Niel, et al.; Colchicine Today; Joint Bone Spine; 73; pp. 672-678; (2006).
Ogbru and Marks (www.medicinenet.com) available on line as of Sep. 8, 2008.
Perez-Ruiz, et al; •Optimisation of the Treatment of Acute Gout; BioDrugs; 13; pp. 415-423; (2000).
Rango (Management of Gout w Colchicine, available on line as of Jul. 5, 2003.
Terkeltaub, et al; "Comparison of Low-Dose vs High-Dose Oral Colchicine Regimens in Patients with Gout Flares-Presentation"; Presentation at the American College of Rheumatology Scientific Meeting, 2008 in San Francisco, CA, Oct. 24-29.
Terkeltaub, Robert A.; •Gout; New England Journal of Medicine; 349; pp. 1647-1655; (2003).
Terkeltaub, et al; "The Clinical Relevance of P-gp and CYP 3A4 on Colchicine Metabolism and Elimination"; Presentation at the American College of Rheumatology Scientific Meeting, 2008 in San Francisco, CA, Oct. 24-29.

(Continued)

Primary Examiner — Sreeni Padmanabhan
Assistant Examiner — Kara R McMillian
(74) Attorney, Agent, or Firm — Cantor Colburn LLP

(57) ABSTRACT

Methods for concomitant administration of colchicine together with one or more second active agents, e.g., ketoconazole and ritonavir, are disclosed. Such methods reduce the dangers commonly associated with such concomitant administration and provide additional benefits. Methods of notifying health care practitioners and patients regarding appropriate dosing for concomitant administration of colchicine together with second active agents are also provided.

9 Claims, 5 Drawing Sheets

OTHER PUBLICATIONS

Van Der Velden, Et Al; •Colchicine-Induced Neuromyopathy in a Patient With Chronic Renal Failure: The Role of Clarithromycin; Netherlands, The Journal of Medicine; 66; pp. 204-206; (2008).

Drugs.Com; "Drug Interactions Between Colchicine and Ketoconazole"; printed Dec. 4, 2009; 2 pages.

Horn, et al.; "Life-Threatening Colchicine Drug Interactions"; Pharmacy Times; pp. 111; (May 2006).

Colcyrs_Prescribing Information, www.colcrys.com/assets/pdf/COLCRYS_Full_Prescribing_Information.pdf; 5 pages; Revised Sep. 2009.

Niel, et al.; "Colchicine Today"; Joint Bone Spine; 73; pp. 672-678; (2006).

Perez-Ruiz, et al.; "Optimisation of the Treatment of Acute Gout"; BioDrugs; 13; pp. 415-423; (2000).

Terkeltaub, Robert A.; "Gout"; The New England Journal of Medicine; 349; pp. 1647-1655; (2003).

Terkeltaub, Robert A.; "Colchicine Update: 2008"; Semin. Arthritis Rheum. 38:411-419; (2009) (e publ. Oct. 29, 2008).

Terkeltaub, et al. (a); "Comparison of Low-Dose vs High-Dose Oral Colchicine Regimens in Patients with Gout Flares"; Presentation at the American College of Rheumatology Scientific Meeting: San Francisco, CA; 23 pages; Oct. 26, 2008.

Terkeltaub, et al. (b); "The Clinical Relevance of P-gp and CYP 3A4 on Colchicine Metabolism and Elimination"; Presentation at the American College of Rheumatology Scientific Meeting; San Francisco; CA; 19 pages; (Oct. 26, 2008).

Ben-Chetrit and Levy; "Colchicine: 1998 Update"; Semin, Arthritis Rheum.; 28:48-59; (1998).

Leikin and Paloucek (eds.); "Colchicine"; Poisoning and Toxicology Handbook; 4th ed.; pp. 216-217; (CRC Press; (2008).

Ketoconazole Tablets UPS; Prescribing Information; Apotex, Inc.; 8 pages; Revised Jul. 2004.

Colchicine-Probenecid; http:///www,healthgrades.com/drug-ratings/drug/sideeffects/2207/colchecine-probenecid; 2 pages; printed Dec. 2, 2009.

MPC0263US, U.S. Appl. No. 12/372,046, NonFinal Office Action dated May 18, 2009, 9 pages.

MPC0263US, U.S. Appl. No. 12/372,046, NonFinal Office Action dated Jul. 14, 2009, 10 pages.

MPC0263US, U.S. Appl. No. 12/372,046, Final Office Action dated Sep. 11, 2009, 24 pages.

Herrewege, et al.; "A Dual Chamber Model of Female Cervical Mucosa for the Study of HIV Transmission and for the Evaluation of Candidate HIV Microbicides"; Antiviral Research; 74; 111-124; (2007).

Hsu, et al; "Ritonavir; Clinical Pharmacokinetics and Interactions with Other Anti-HIV Agents"; Clinical Pharmacokinet; 35; pp. 275-291; (1998).

Krishnan et al; "Gout in Ambulatory Care Settings in the United States"; Journal of Rheumatology; 35; pp. 498-501; (2008).

Van Der Velden, Et Al; "Colchicine-Induced Neuromyopathy in a Patient With Chronic Renal Failure: The Role of Clarithromycin"; Netherlands, The Journal of Medicine; 66; pp. 204-206; (2008).

Zhou, et. al; "Clinical Outcomes and Management of Mechanism-Based Inhibition of Cytochrome P450 3A4"; Therapeutics and Clinical Risk Management; 1; pp. 3-13; (2005).

MPC0263US, U.S. Appl. No. 12/372,046, NonFinal Office Action dated Jan. 26, 2010, 30 pages.

Creighton, et al.; "IS Ritonavir Boosting Associated with Gout?"; Royal Society of Medicine Services, London, U.K.; 16; pp. 362-364; (2005).

Lacy et al. Lexi-Comp's Clinical Reference Library, Drug Information Handbook, 7th Edition, 1999-2000), pp. 108-109 and 292-293.

Rangno, Robert; "Management of Gout With Colchicine"; available on line as of Jul. 5, 2003; http://www.theberries.ca/Archives/colchicine.html; 4 pages.

Colchicine Indications and Dosage; available online at http://rx-s.net/weblog/more/colchicine-indications-and-dosage/; last revised Aug. 2, 2005.

Wang et al.; "HMG-CoA Reductase Inhibitors (Statins) Characterized as Direct Inhibitors of P-Glycoprotein"; Pharmaceutical Research; 18; pp. 800-806; (2001).

U.S. Appl. No. 12/688,038, filed Jan. 15, 2010, Non-Final Office Action dated Apr. 2, 2010; 43 pages.

U.S. Appl. No. 12/688,038, filed Jan. 15, 2010, Final Office Action dated Jun. 28, 2010, 33 pages.

"Colchicine Dosage"; http://www.drugs.com/dosage/colchicine.html; 6 pages.

Ogbru and Marks; "Medications and Drugs"; MedicineNet.com; http://www.medicinenet.com/colchicine/article.htm; 2 pages; (2008).

Achert et al.; "Pharmacokinetics/bioavailability of colchicine in healthy male volunteers"; European Journal of Drug Metabolism and Pharmacokinetics; 14(4); pp. 317-322; (1989).

Ahern et al., "Does Colchicine Work? The results of the first controlled study in acute gout"; Aust NZ J Med 1987; 17:301-304.

Brooks; "Rheumatic Disorders" Chapter 25 of Avery's Drug Therapy, Pub. 1997 by Adis International, pp. 1113-1161.

Dahan et al., "Grapefruit Juice and its Constituents Augment Colchicine Intestinal Absorption: Potential Hazardous Interaction and the Role of P-Glycoprotein", Pharm Res. 2009; 26(4); 883-92; Epub Dec. 2, 2008.

Goldbart, et al.; Near Fatal Acute Colchicine Intoxication in a Child. A Case Report; Eur J Pediatr; 159; pp. 895-897; (2000).

"Guidance for Industry—In Vivo Drug Metabolism/Drug Interaction Studies—Study Design, Data Analysis, and Recommendations for Dosing and Labeling"; 19 pages; USDA; Nov. 1999.

"Risk of Drug Interactions Involving Herbval and Citrus Products"; Health Canada International Symposium on Drug, Food and Natural Health Product Interactions; Gatineau, Quebec, 61 pages; powerpoint presentation; Feb. 9, 2006.

Sabouraud, et al.; "Pharmacokinetics of Colchicine: A Review of Experimental and Clinical Data"; 2 Gastroenterol (Suppl. 1); 30; pp. 35-39 (1992).

\* cited by examiner

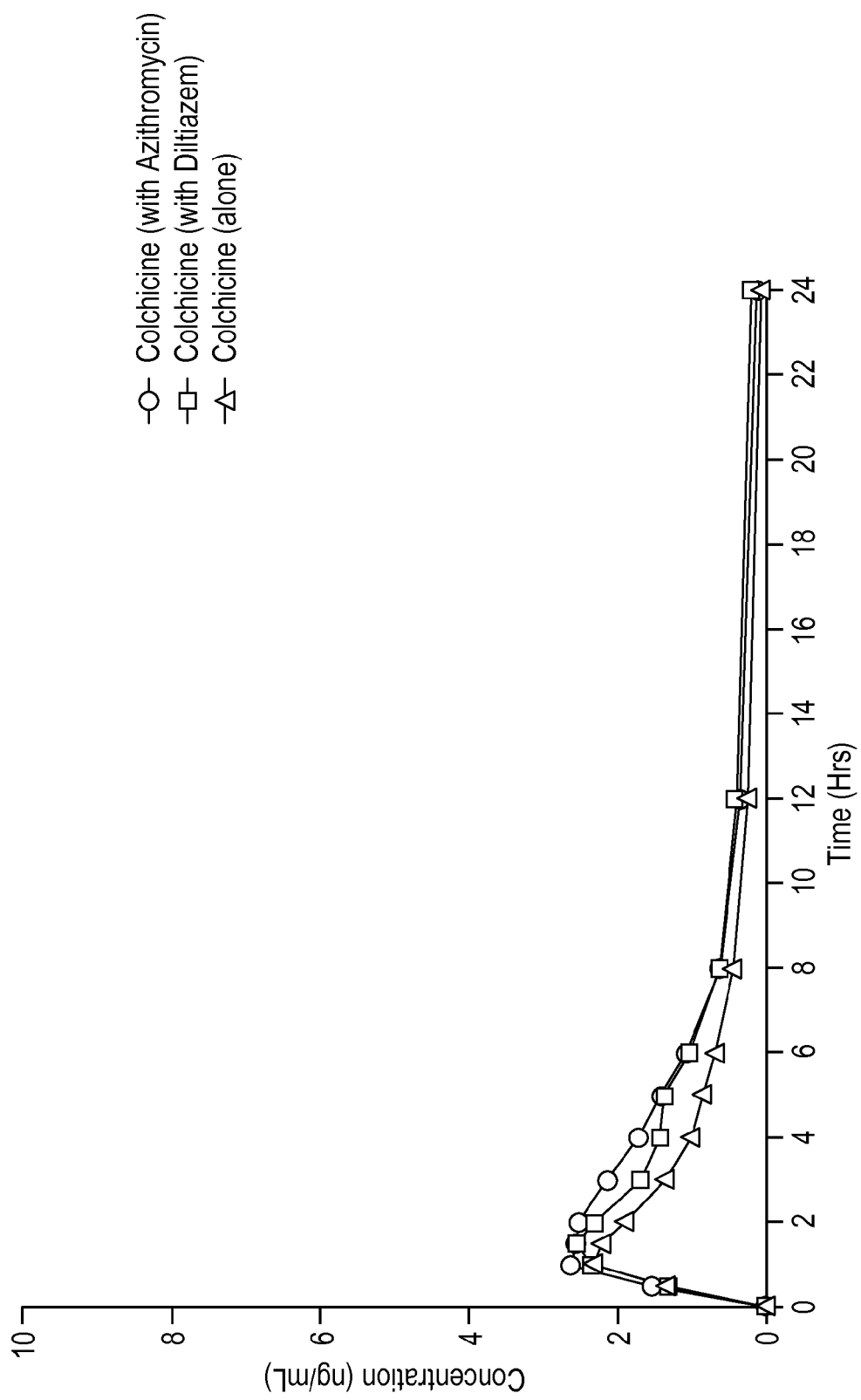

US 8,093,297 B2

METHODS FOR CONCOMITANT ADMINISTRATION OF COLCHICINE AND A SECOND ACTIVE AGENT

CROSS REFERENCE TO RELATED APPLICATIONS

This application is a Continuation U.S. application Ser. No. 12/909,171, filed Oct. 21, 2010, which is a continuation of U.S. application Ser. No. 12/372,046, filed Feb. 17, 2009, now U.S. Pat. No. 7,820,681, which claims priority from U.S. Provisional Application Ser. Nos. 61/138,141 filed Dec. 17, 2008 and 61/152,067 filed Feb. 12, 2009, all of which are hereby incorporated by reference in their entirety.

FIELD OF THE DISCLOSURE

This disclosure relates to methods allowing for the co-administration of colchicine together with one or more second active agents for therapeutic purposes with improved safety compared to prior methods of administration.

BACKGROUND

Colchicine, chemical name (−)-N-[(7S,12aS)-1,2,3,10-tetramethoxy-9-oxo-5,6,7,9-tetrahydrobenzo[a]heptalen-7-yl]-acetamide, is an alkaloid found in extracts of *Colchicum autumnale, Gloriosa superba*, and other plants. It is a microtubule-disrupting agent used in the treatment of gout and other conditions that may be treated, relieved or prevented with anti-inflammatory treatment. Colchicine impairs the motility of granulocytes and can prevent the inflammatory phenomena that initiate an attack (or flare) of gout. Colchicine also inhibits mitosis, resulting in effects in cells with high turnover rates such as those in the gastrointestinal tract and bone marrow. The primary adverse side effects of colchicine therapy include gastrointestinal upset such as diarrhea and nausea.

Colchicine has a narrow therapeutic index. The margin between an effective dose and a toxic dose of colchicine is much narrower than that of many other widely used drugs. Consequently, actions that result in increased colchicine levels in patients receiving colchicine therapy are particularly dangerous. Co-administration of colchicine to patients along with certain other drugs can have the effect of increasing colchicine levels. Such drug-drug interactions with colchicine have been reported to result in serious morbid complications and, in some cases, death.

Colchicine is rapidly absorbed from the gastrointestinal tract. Peak concentrations occur in 0.5 to 2 hours. The drug and its metabolites are distributed in leukocytes, kidneys, liver, spleen and the intestinal tract. Colchicine is metabolized in the liver and excreted primarily in the feces with 10 to 20% eliminated unchanged in the urine.

Gout (or gouty arthritis) is a disease caused by a build up of uric acid in the joints. Such a build up is typically due to an overproduction of uric acid, or to a reduced ability of the kidney to excrete uric acid. Gout is characterized by excruciating, sudden, unexpected, burning pain, as well as by swelling, redness, warmness, and stiffness in the affected joint. Low-grade fever may also be present. A gout flare is a sudden attack of pain in affected joints, especially in the lower extremities, and most commonly in the big toe. In afflicted individuals, the frequency of gout flares typically increases over time. In this manner, gout progresses from acute gout to chronic gout, which involves repeated episodes of joint pain.

Colchicine can reduce pain in attacks of acute gout flares and also can be used beneficially for treating adults for prophylaxis of gout flares. Although its exact mode of action in the relief of gout is not completely understood, colchicine is known to decrease the inflammatory response to urate crystal deposition by inhibiting migration of leukocytes, to interfere with urate deposition by decreasing lactic acid production by leukocytes, to interfere with kinin formation and to diminish phagocytosis and subsequent inflammatory responses.

Cytochrome p450 (CYP) enzymes are agents of drug metabolism that are found in the liver, the gastrointestinal tract and other locations in the body. CYP enzymes occur in a variety of closely related proteins referred to as isozymes and different CYP isozymes may preferentially metabolize different drugs. The 3A family of CYP isozymes, particularly CYP3A4, is also known to be involved in many clinically significant drug-drug interactions, including those involving colchicine and second active agents. While drugs are often targets of CYP-mediated metabolism, some may also alter the expression and activity of such enzymes, thus impacting the metabolism of other drugs. The biotransformation of colchicine in human liver microsomes involves formation of 3-demethylchochicine and 2-demethylcolchicine. As shown by experiments using antibodies against CYP3A4 and experiments using chemical inhibition of CYP3A4, this transformation is correlated with (and thus apparently mediated by) CYP3A4 activity.

P-glycoprotein (P-gp) is an ATP-dependent cell surface transporter molecule that acts as an ATPase efflux pump for multiple cytotoxic agents, including colchicine. P-gp actively pumps certain compounds, including drugs such as colchicine, out of cells. P-gp is encoded by the Adenosine triphosphate-binding cassette subfamily B member 1 (ABCB1) gene, also referred to as the multiple drug resistance 1 gene (MDR1).

Since colchicine acts intracellularly, the combined effects of CYP3A4 inhibition and P-gp inhibition by second active agents that also interact with CYP3A4 and P-gp can cause colchicine toxicity in patients taking what would be a safe dose of colchicine in the absence of concomitant second agent administration. Various studies of adverse reactions from exposure to multiple drugs have found that 6.5-23% of the adverse reactions result from drug-drug interactions. Unfortunately, each year a number of deaths occur as the direct result of patients adding a concomitant prescription pharmaceutical product to their existing medication regimen.

There accordingly remains a need for improved methods for administering colchicine to individuals who are concomitantly being treated with second active agents so as to reduce the possibility of colchicine toxicity while maintaining the sometimes life-saving advantages of being able to administer the two (or more) agents concomitantly. The present disclosure addresses this need and provides further advantages.

SUMMARY

In one embodiment, a method of treating an individual in need of treatment with colchicine comprises concomitantly administering to the individual colchicine and another drug, for example, ketoconazole or ritonavir or cyclosporine, wherein the colchicine is administered as a dosing regimen with a starting colchicine dose of no more than about 0.6 mg colchicine, followed by either: no additional colchicine doses within about 12, 24, 48, or 72 hours, or at least one additional colchicine dose within about 12 hours and no more frequently than once every hour wherein each additional colchicine dose is no greater than about 0.6 mg. According to another embodiment, the other drug is, for example, verapamil or diltiazem, and the starting colchicine dose during coadministration with the other drug is no more than about 1.2 mg colchicine, followed by either: no additional colchicine doses within about 12, 24, 48, or 72 hours, or at least one additional colchicine dose within about 12 hours.

In another aspect, a method of using colchicine comprises increasing the blood plasma levels of colchicine in a individual being administered doses of about 0.6 mg or less of colchicine to treat a colchicine-treatable condition, said method comprising the concomitant dosing of the individual with a sufficient amount of ketoconazole to increase the $C_{max}$ of colchicine by about 90%, or to increase the $AUC_{0-t}$ of colchicine in the individual by about 190%, or to increase the $AUC_{0-inf}$ of colchicine in the individual by about 205%, or to decrease the clearance of colchicine by about 70%, compared to the $C_{max}$, $AUC_{0-t}$, $AUC_{0-inf}$, or clearance in a matched individual not administered concomitant ketoconazole.

In yet another aspect, a method of using colchicine comprises increasing the blood plasma levels of colchicine in an individual being administered doses of about 0.6 mg or less of colchicine to treat a colchicine-treatable condition, said method comprising the concomitant dosing of the individual with a sufficient amount of ritonavir to increase the $C_{max}$ of colchicine by about 170%, or to increase the $AUC_{0-t}$ of colchicine in the individual by about 245%, or to decrease the clearance of colchicine by about 70%, compared to the $C_{max}$, $AUC_{0-t}$, or clearance in a matched individual not administered concomitant ritonavir.

In another embodiment, a method for using colchicine comprises a pharmacy receiving a prescription for colchicine for a patient who is concomitantly being treated with ketoconazole or ritonavir or verapamil, and the pharmacy dispensing colchicine in response to receipt of the prescription, wherein the dispensing is preceded by: entering, into a first computer readable storage medium in functional communication with a computer, of a unique patient identifier for said patient and at least one drug identifier for colchicine linked to the patient identifier so as to indicate that colchicine is to be administered to the patient, wherein the computer has been programmed to issue a drug-drug interaction alert when the at least one drug identifier for colchicine is entered linked to the patient identifier so as to indicate that colchicine is to be administered to the patient and when the patient identifier is also linked to an identifier indicating that ketoconazole or ritonavir or verapamil is being concomitantly administered to the patient, wherein, upon entry of the at least one drug identifier for colchicine linked to the patient identifier, a drug-drug interaction alert is issued to one or more of a pharmacy technician, a pharmacist, or a pharmacy customer obtaining the colchicine, said alert indicating that that ketoconazole or ritonavir is being concomitantly administered to the patient and that prior to the colchicine being dispensed, the colchicine dosing regimen must be reviewed and, if necessary adjusted, so that when the colchicine is delivered to the pharmacy customer obtaining the colchicine it is delivered along with instructions for the colchicine to be taken in accordance with a dosing regimen of no more than about 0.6 mg colchicine, followed by either: no additional colchicine doses within about 12, 24, 48, or 72 hours, or at least one additional colchicine dose within about 12 hours and no more frequently than once every hour wherein each additional colchicine dose is no greater than about 0.6 mg.

A method of treating a patient with colchicine comprises administering an adjusted daily dosage amount of colchicine to the patient who is receiving concomitant administration of ritonavir, wherein the adjusted daily dosage amount of colchicine is about 25% to 50% of an intended daily dosage amount of colchicine, and wherein the intended daily dosage amount of colchicine is a dose suitable for the patient if the patient were not receiving concomitant ritonavir.

A method of treating a patient with colchicine comprises administering an adjusted daily dosage amount of colchicine to the patient who is receiving concomitant administration of ketoconazole, wherein the adjusted daily dosage amount of colchicine is about 25% to 50% of an intended daily dosage amount of colchicine, and wherein the intended daily dosage amount of colchicine is a daily dosage amount suitable for the patient if the patient were not receiving concomitant ketoconazole.

A method of treating an individual in need of treatment for gout flares, comprises concomitantly administering colchicine and azithromycin, and carefully monitoring the individual for potential toxicity. The method further comprises adjusting the dose of colchicine or azithromycin as necessary to avoid adverse side effects.

A method of treating an individual with colchicine comprises concomitantly administering colchicine and verapamil, and carefully monitoring the individual for signs and symptoms of adverse side effects. The method further comprises administering an adjusted daily dosage amount of colchicine to the patient who is receiving concomitant administration of verapamil, wherein the adjusted daily dosage amount of colchicine is about 50% to 75% of an intended daily dosage amount of colchicine, and wherein the intended daily dosage amount of colchicine is a daily dosage amount suitable for a patient if the patient were not receiving concomitant verapamil.

BRIEF DESCRIPTION OF THE DRAWINGS

FIG. 5 shows a pharmacokinetic profile comparison of single-dose colchicine (0.6 mg, alone) and single-dose colchicine (0.6 mg) co-administered with steady-state azithromycin and steady-state diltiazem in healthy adults. Y axis=colchicine concentration, ng/mL, X axis=time in hours, N=18, ▲=colchicine alone, •=colchicine plus azithromycin, ■=colchicine plus diltiazem.

DETAILED DESCRIPTION

Figure 1:
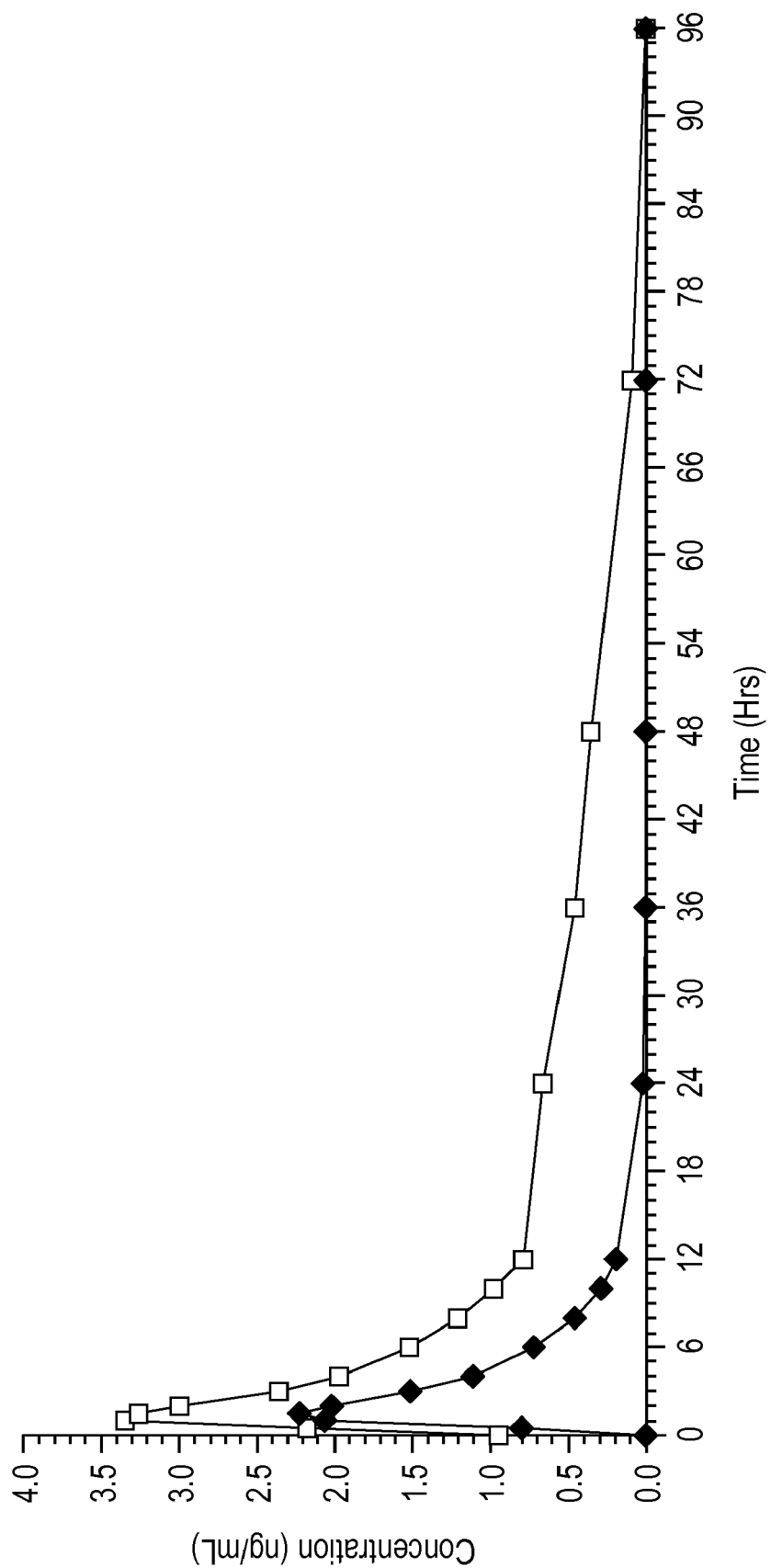
FIG. 1 shows mean colchicine plasma concentrations following administration of single and multiple oral doses of colchicine 0.6 mg in healthy adults, N=13, Y axis=colchicine concentration, ng/mL, X axis=time in hours, ♦=day 1, □=day 25. See Example 1.

Disclosed herein are methods for safely administering colchicine concomitantly with a second active agent, wherein the second active agent is a CYP3A4 inhibitor, a P-gp inhibitor, or both. Exemplary second active agents that are CYP3A4 and P-gp inhibitors are azithromycin, ketoconazole, ritonavir, diltiazem, verapamil and cyclosporine. It has now been discovered that certain reduced or limited colchicine dosage amounts, when administered with concomitantly administered recommended dosage amounts of second active agents that are CYP3A4 inhibitors, P-gp inhibitors, or both, achieve plasma colchicine levels that are therapeutically effective, but are not significantly higher, and therefore not significantly more toxic, than plasma levels achieved by administration of manufacturers' recommended colchicine dosages in the absence of concomitant administration with the second active agent. Thus, colchicine and second active agents that are CYP3A4 inhibitors, P-gp inhibitors, or both, can be administered concomitantly with improved safety when colchicine is administered as disclosed herein.

Without being held to theory, it has been hypothesized by the inventors herein that P-gp inhibition is more important in the elimination of colchicine than CYP3A4 inhibition. The CYP3A4 and P-gp inhibition potential of clarithromycin, azithromycin, ketoconazole, ritonavir, diltiazem and cyclosporine are given in Table 1. Based on their level of P-gp inhibition, it was predicted that clarithromycin and cyclosporine will increase colchicine concentrations more than ketoconazole or ritonavir, which will increase colchicine levels more than verapamil, azithromycin or diltiazem. The results presented herein confirm this hypothesis.

TABLE 1

CYP3A4 and P-gp inhibition potential of second active agents

| Drug | CYP3A Inhibition potential | P-gp Inhibition potential |
|---|---|---|
| Clarithromycin | +++++ | +++++ |
| Cyclosporine | +++++ | +++++ |
| Ketoconazole | +++++ | +++ |
| Ritonavir | +++++ | +++ |
| Verapamil | ++ | ++ |
| Diltiazem | + | + |
| Azithromycin | + | + |

Ritonavir (Norvir®, Abbott Laboratories) is an inhibitor of Human Immunodeficiency Virus (HIV) protease and is approved for the treatment of HIV-infection when used as part of a highly active antiretroviral therapy (HAART) regimen at the recommended dose of 600 mg twice daily. Although a very potent and effective protease inhibitor at the recommended dose, ritonavir is not well tolerated by HIV-infected patients at the approved dose and therefore, is generally not used clinically as a sole, therapeutic protease inhibitor within a HAART regimen. Rather, ritonavir is used more often as a pharmacokinetic enhancer or 'boosting agent' when combined with other approved protease inhibitors that are CYP3A4 and P-gp substrates and also have inherent bioavailability issues, such as poor bioavailability due to first pass effect. Improving the pharmacokinetic disposition of other protease inhibitors is possible due to the potent CYP3A4 and P-gp inhibitory activity ritonavir possesses. Sub-therapeutic ritonavir doses are used to achieve pharmacokinetic enhancement of the co-administered protease inhibitors; typically 100 mg of ritonavir administered twice daily is the ritonavir dose used in combination with the primary protease inhibitor. This low-dose ritonavir regimen boosts the bioavailability of the second protease inhibitor without contributing significantly to the adverse event profile of the HAART regimen.

Cyclosporine (Neoral®, Novartis Pharmaceuticals Corporation) is the active principle in Neoral® an oral formulation that immediately forms a microemulsion in an aqueous environment. Cyclosporine is indicated for kidney, liver, and heart transplantation; rheumatoid arthritis and psoriasis. Cyclosporine is extensively metabolized by the CYP3A4 enzyme system in the liver, and to a lesser degree in the gastrointestinal tract, and the kidney. The metabolism of cyclosporine can be altered by the co-administration of a variety of agents.

Ketoconazole is a synthetic broad-spectrum antifungal agent available in scored white tablets, each containing 200 mg ketoconazole base for oral administration. Ketoconazole tablets are indicated for the treatment of the following systemic fungal infections: candidiasis, chronic mucocutaneous candidiasis, oral thrush, candiduria, blastomycosis, coccidioidomycosis, histoplasmosis, chromomycosis, and paracoccidioidomycosis. Ketoconazole is a potent inhibitor of the CYP3A4 enzyme system. Co-administration of ketoconazole and drugs primarily metabolized by the CYP3A4 enzyme may result in increased plasma concentrations of the drugs that could increase or prolong both therapeutic and adverse side effects.

Azithromycin is a macrolide antibiotic indicated for the treatment of patients with mild to moderate infections caused by susceptible strains of the designated microorganisms in specific conditions. Azithromycin remains the sole agent developed and marketed within the azalide macrolide subclass. Due to its dibasic structure, azithromycin has demonstrated unique pharmacokinetic properties that differ significantly from those of classic macrolide agents. Azithromycin's pharmacokinetics are characterized by low concentrations in serum, secondary to rapid and significant uptake by fibroblasts and acute reactant cells such as polymorphonuclear leukocytes (PMNs), monocytes, and lymphocytes. Azithromycin is a weak to moderate CYP3A4 inhibitor.

Diltiazem (Cardizem® CD, Biovail Pharmaceuticals, Inc. [Biovail]) is an extended-release (ER) calcium ion influx inhibitor available in blue capsules, each containing 240 mg diltiazem hydrochloride for oral administration. Diltiazem ER capsules are indicated for the treatment of hypertension and the management of chronic stable angina and angina due to coronary artery spasm. Diltiazem is a CYP3A4 and P-gp inhibitor.

Verapamil HCl ER (Mylan Pharmaceuticals, Inc.) is a calcium ion influx inhibitor available in a pale green, capsule shaped, film-coated tablets, each containing 240 mg verapamil hydrochloride for oral administration. Verapamil HCl ER tablets are indicated for the management of hypertension. Verapamil HCl ER is a potent CYP3A4 and P-gp inhibitor.

In one embodiment, colchicine is administered to an individual suffering from a condition treatable with colchicine, and the concomitant second active agent (e.g., ketoconazole, ritonavir, cyclosporine, verapamil, or diltiazem or any other CYP3A4 or P-gp inhibitor) is administered concurrently while the colchicine administration is reduced, or the individual has recently completed a dosing regimen of the second active agent, in which case the colchicine administration may still be reduced for a period of time.

In one embodiment, disclosed herein is a method of administering colchicine and a second active agent (e.g., ketoconazole, ritonavir, or cyclosporine) wherein an individual is administered the colchicine according to a colchicine dosing regimen of a single starting colchicine dose of no more than about 0.6 mg colchicine, followed by either no additional colchicine doses within about 12, 24, 48, or 72 hours, or followed by at least one additional colchicine dose within 12 hours and no more frequently than once every hour (e.g., every 3, 4, 6, 8, or 12 hours). In this embodiment, each additional colchicine dose is specifically no greater than about 0.3 mg and the individual is an adult individual or a pediatric individual. Specifically, the starting colchicine dose is about 0.6 mg or about 0.3 mg, and each additional colchicine dose is about 0.3 mg. In one embodiment, when additional doses are administered, only two, three, or four additional colchicine doses are administered within about 24 hours. Specifically, the individual is an adult individual and the starting colchicine dose is about 0.6 mg, and each additional colchicine dose, if any, is about 0.3 mg. In one embodiment, only three additional colchicine doses are administered within about 24 hours.

In one embodiment, disclosed herein is a method of administering colchicine and a second active agent (e.g., verapamil or diltiazem) wherein an individual is administered the colchicine according to a colchicine dosing regimen of a single starting colchicine dose of no more than about 1.2 mg colchicine, followed by either no additional colchicine doses within about 12, 24, 48, or 72 hours, or followed by at least one additional colchicine dose within 12 hours and no more frequently than once every hour (e.g., every 3, 4, 6, 8, or 12 hours). In this embodiment, each additional colchicine dose is specifically no greater than about 0.3 mg or 0.6 mg and the individual is an adult individual or a pediatric individual. Specifically, the starting colchicine dose is about 0.6 mg or 1.2 mg, and each additional colchicine dose is about 0.3 mg or 0.6 mg. In one embodiment, when additional doses are administered, only two, three, or four additional colchicine doses are administered within about 24 hours. Specifically, the individual is an adult individual and the starting colchicine dose is about 1.2 mg, and each additional colchicine dose, if any, is about 0.3 mg or 0.6 mg. In one embodiment, only three additional colchicine doses are administered within about 24 hours.

In one embodiment, the second active agent is ketoconazole or ritonavir. In one embodiment, the ketoconazole is administered to the individual at a dosage of about 200 mg daily and the colchicine dosing regimen is one about 0.6 mg colchicine dose to start, followed by 0, 1, 2, 3, or 4 additional colchicine doses of about 0.6 mg every 1, 2, 3, 4, 5, 6, 7, 8, 9, 10, 11, or 12 hours (e.g., every 2, 3, 4, 5, or 6 hours) after the preceding colchicine dose. In another embodiment, the ritonavir is administered to the individual at a dosage of about 200 to 1200 mg daily (e.g., in 2×100 mg doses or 2×600 mg doses) and the colchicine dosing regimen is one about 0.6 mg colchicine dose to start, followed by 0, 1, 2, 3, or 4 additional colchicine doses of about 0.6 mg every 1, 2, 3, 4, 5, 6, 7, 8, 9, 10, 11, or 12 hours (e.g., every 2, 3, 4, 5, or 6 hours) after the preceding colchicine dose. In an exemplary regimen for treatment of acute gout flares, ingestion of colchicine is continued until a total of no more than about 1.2, 1.4, 1.6, 1.8, 2, or 2.4 mg of colchicine has been ingested, after which ingestion of colchicine is stopped until a subsequent acute gout flare occurs. More preferably, the colchicine is administered as a dosage form of 0.6 mg (e.g., one 0.6 mg colchicine tablet), or 0.3 mg (e.g., one half of a 0.6 mg tablet) of colchicine and administration of the dosage form is not repeated within a period of at least about two days, preferably at least about three days.

In one embodiment, the second active agent (e.g., ketoconazole or ritonavir or cyclosporine) is administered to the individual before the colchicine is administered to the individual, and wherein the administration of second active agent is terminated no more than about fourteen days prior to the initiation of colchicine administration. For example, the method comprises administering colchicine to an individual also taking a second active agent (e.g., ketoconazole or ritonavir or cyclosporine), or having completed treatment with the second active agent within the prior 14 days, the individual being administered a single dose of about 0.6 mg or about 0.3 mg of colchicine to treat a gout flare, which administration is not repeated within any 3-day period. According to this embodiment if the second active agent is instead verapamil or diltiazem, if the second active agent is terminated no more than about fourteen days prior to the initiation of the colchicine administration to treat a gout flare, the single dose of colchicine is about 1.2 mg not to be repeated within a 3-day period.

In another aspect, herein disclosed is a method for increasing the blood plasma levels of colchicine in an individual to whom colchicine is being administered to treat or prevent a colchicine-responsive condition. This method comprises the concomitant dosing of the individual with a sufficient amount of ketoconazole to increase the $C_{max}$ of colchicine by about 90%, or to increase the $AUC_{0-t}$ of colchicine in the individual by about 190%, or to increase the $AUC_{0-inf}$ of colchicine in the individual by about 205%, or to decrease the clearance of colchicine by about 70%, compared to the $C_{max}$, $AUC_{0-t}$, or clearance in the same or a matched individual when not being administered a concomitant ketoconazole. In a specific embodiment, the individual is being administered no more than hourly doses of about 0.6 mg of colchicine or less, and the amount of ketoconazole is about 200 mg. In one embodiment, the single dose is one 0.6 mg colchicine tablet.

In yet another aspect, herein disclosed is a method for increasing the blood plasma levels of colchicine in an individual to whom colchicine is being administered to treat or prevent a colchicine-responsive condition. This method comprises the concomitant dosing of the individual with a sufficient amount of ritonavir to increase the $C_{max}$ of colchicine by about 170%, or to increase the $AUC_{0-t}$ of colchicine in the individual by about 245%, or to decrease the clearance of colchicine by about 70%, compared to the $C_{max}$, $AUC_{0-t}$, or clearance in the same or a matched individual when not being administered concomitant ritonavir. In a specific embodiment, the individual is being administered no more than hourly doses of about 0.6 mg of colchicine or less, and the amount of ritonavir is about 200 to about 1200 mg. In one embodiment, the single dose is one 0.6 mg colchicine tablet.

In one embodiment, a method of treating a patient with colchicine comprises administering an adjusted daily dosage amount of colchicine to the patient who is receiving concomitant administration of ritonavir, wherein the adjusted daily dosage amount of colchicine is 25% to 50% of an intended daily dosage amount of colchicine, and wherein the intended daily dosage amount of colchicine is a daily dosage amount suitable for the patient if the patient were not receiving concomitant ritonavir. Treating is, for example, to prevent gout flares, to treat acute gout, or to treat familial Mediterranean fever. When the colchicine is administered to prevent gout flares, the adjusted daily dosage amount of colchicine may reduced from a 0.6 mg twice daily intended dose to a 0.6 mg once daily adjusted dose. Alternatively, when the colchicine is administered to prevent gout flares, wherein the adjusted daily dosage amount of colchicine is reduced from a 0.6 mg once daily intended dose to a 0.3 mg once daily adjusted dose.

In one embodiment, when treating is for acute gout, the intended daily dosage amount is 1.8 to 2.4 mg, and the maximum adjusted daily dosage amount is 0.6 mg, not to be repeated within 3 days. In another embodiment, treating is for acute gout, the intended daily dosage amount is 2.4 to 4.8 mg and the maximum adjusted daily dosage amount is 0.6 to 1.2 mg, not to be repeated within 3 days. In yet another embodiment, treating is for familial Mediterranean fever and the daily dosage amount 1.2 to 2.4 mg for adults, and the maximum adjusted daily dosage amount is 0.6 mg, given, for example, in two 0.3 mg doses. In another embodiment, treating is for familial Mediterranean fever and the intended daily dosage amount is 0.9 to 1.8 mg for children 6-12 years or 4-6 years, and the maximum adjusted daily dosage amount is 0.6 mg, given, for example, in two 0.3 mg doses. The concomitantly administered dose of ritonavir is, for example, 200 mg per day. In one embodiment, the ritonavir is administered to the patient before the colchicine is administered to the patient, and wherein the administration of ritonavir is terminated no more than about fourteen days prior to the initiation of colchicine administration. The method optionally further comprises carefully monitoring the individual for potential toxicity. Any 0.3 mg dose contemplated in this method can be a single 0.3 mg dosage form or one-half a 0.6 mg dosage form, e.g. one-half a 0.6 mg colchicine tablet.

A method of treating a patient with colchicine comprises administering an adjusted daily dosage amount of colchicine to the patient who is receiving concomitant administration of ketoconazole, wherein the adjusted daily dosage amount of colchicine is 25% to 50% of an intended daily dosage amount of colchicine, and wherein the intended daily dosage amount of colchicine is a daily dosage amount suitable for the patient if the patient were not receiving concomitant ketoconazole. Treating is, for example, to prevent gout flares, to treat acute gout, or to treat familial Mediterranean fever. When the colchicine is administered to prevent gout flares, the adjusted daily dosage amount of colchicine may reduced from a 0.6 mg twice daily intended dose to a 0.6 mg once daily adjusted dose. Alternatively, when the colchicine is administered to prevent gout flares, wherein the adjusted daily dosage amount of colchicine is reduced from a 0.6 mg once daily intended dose to a 0.3 mg once daily adjusted dose. In one embodiment, when treating is for acute gout, the intended daily dosage amount is 1.8 to 2.4 mg, and the maximum adjusted daily dosage amount is 0.6 mg, not to be repeated within 3 days. In another embodiment, treating is for acute gout, the intended daily dosage amount is 2.4 to 4.8 mg and the maximum adjusted daily dosage amount is 0.6 to 1.2 mg, not to be repeated within 3 days. In yet another embodiment, treating is for familial Mediterranean fever and the daily dosage amount 1.2 to 2.4 mg for adults, and the maximum adjusted daily dosage amount is 0.6 mg, given, for example, in two 0.3 mg doses. In another embodiment, treating is for familial Mediterranean fever and the intended daily dosage amount is 0.9 to 1.8 mg for children 6-12 years or 4-6 years, and the maximum adjusted daily dosage amount is 0.6 mg, given, for example, in two 0.3 mg doses. The concomitantly administered dose of ketoconazole is, for example, 250 mg per day. In one embodiment, the ketoconazole is administered to the patient before the colchicine is administered to the patient, and wherein the administration of ketoconazole is terminated no more than about fourteen days prior to the initiation of colchicine administration. The method optionally further comprises carefully monitoring the individual for potential toxicity. Any 0.3 mg dose contemplated in this method can be a single 0.3 mg dosage form or one-half a 0.6 mg dosage form, e.g. one-half a 0.6 mg colchicine tablet.

A method of treating a patient with colchicine comprises administering an adjusted daily dosage amount of colchicine to the patient who is receiving concomitant administration of cyclosporine, wherein the adjusted daily dosage amount of colchicine is 25% to 50% of an intended daily dosage amount of colchicine, and wherein the intended daily dosage amount of colchicine is a daily dosage amount suitable for the patient if the patient were not receiving concomitant cyclosporine. Treating is, for example, to prevent gout flares, to treat acute gout, or to treat familial Mediterranean fever. When the colchicine is administered to prevent gout flares, the adjusted daily dosage amount of colchicine may reduced from a 0.6 mg twice daily intended dose to a 0.3 mg once daily adjusted dose. Alternatively, when the colchicine is administered to prevent gout flares, wherein the adjusted daily dosage amount of colchicine is reduced from a 0.6 mg once daily intended dose to a 0.3 mg once every other day adjusted dose. In one embodiment, when treating is for acute gout, the intended daily dosage amount is 1.8 to 2.4 mg, and the maximum adjusted daily dosage amount is 0.6 mg, not to be repeated within 3 days. In another embodiment, treating is for acute gout, the intended daily dosage amount is 2.4 to 4.8 mg and the maximum adjusted daily dosage amount is 0.6 to 1.2 mg, not to be repeated within 3 days. In yet another embodiment, treating is for familial Mediterranean fever and the daily dosage amount 1.2 to 2.4 mg for adults, and the maximum adjusted daily dosage amount is 0.6 mg, given, for example, in two 0.3 mg doses. In another embodiment, treating is for familial Mediterranean fever and the intended daily dosage amount is 0.9 to 1.8 mg for children 6-12 years or 4-6 years, and the maximum adjusted daily dosage amount is 0.6 mg, given, for example, in two 0.3 mg doses. The concomitantly administered dose of cyclosporine can be various dosage strengths administered per day, and can be administered as an oral preparation, topically, or intravenously. In one embodiment, the cyclosporine is administered to the patient before the colchicine is administered to the patient, and wherein the administration of cyclosporine is terminated no more than about fourteen days prior to the initiation of colchicine administration. The method optionally further comprises carefully monitoring the individual for potential toxicity. Any 0.3 mg dose contemplated in this method can be a single 0.3 mg dosage form or one-half a 0.6 mg dosage form, e.g. one-half a 0.6 mg colchicine tablet.

In another embodiment, colchicine is concomitantly administered with azithromycin. Concomitant administration of azithromycin with colchicine increases exposure to colchicine approximately 46% and thus has the potential to produce colchicine toxicity. During concomitant use of azithromycin and colchicine, the physician should carefully monitor individuals for any signs or symptoms of colchicine toxicity. Additionally, dosing adjustments to either the colchicine and/or the azithromycin may be necessary to avoid adverse side effects.

A method of treating a patient with colchicine comprises administering an adjusted daily dosage amount of colchicine to the patient who is receiving concomitant administration of verapamil, wherein the adjusted daily dosage amount of colchicine is 50% to 75% of an intended daily dosage amount of colchicine, and wherein the intended daily dosage amount of colchicine is a daily dosage amount suitable for the patient if the patient were not receiving concomitant verapamil. Treating is, for example, to prevent gout flares, to treat acute gout, or to treat familial Mediterranean fever. When the colchicine is administered to prevent gout flares, the adjusted daily dosage amount of colchicine may reduced from a 0.6 mg twice daily intended dose to a 0.3 mg once daily adjusted dose. In one embodiment, when treating is for acute gout, the intended daily dosage amount is 1.8 to 2.4 mg, and the maximum adjusted daily dosage amount is 1.2 mg. In another embodiment, treating is for acute gout, the intended daily dosage amount is 2.4 to 4.8 mg and the maximum adjusted daily dosage amount is about one-third the intended daily dosage amount. In yet another embodiment, treating is for familial Mediterranean fever and the daily dosage amount 1.2 to 2.4 mg for adults, and the maximum adjusted daily dosage amount is 1.2 mg, given, for example, in two 0.6 mg doses. In one embodiment, the verapamil is administered to the patient before the colchicine is administered to the patient, and wherein the administration of verapamil is terminated no more than about fourteen days prior to the initiation of colchicine administration. The method optionally further comprises carefully monitoring the individual for potential toxicity. Any 0.3 mg dose contemplated in this method can be a single 0.3 mg dosage form or one-half a 0.6 mg dosage form, e.g. one-half a 0.6 mg colchicine tablet.

Disclosed herein are specific dosage reductions of colchicine that improve safety when colchicine is co-administered with certain active agents. The dose of colchicine recommended for administration without co-administration of certain other active agents, such as CYP3A4 or P-gp inhibitors, is referred to as an intended daily dosage amount. The reduced or modified daily dosage amount determined from the experiments presented herein is referred to as an adjusted daily dosage amount. An adjusted daily dosage amount is thus a daily dosage amount that can be safely co-administered with a second active agent as disclosed herein. A dose adjustment is thus a dose of colchicine and does not include cessation of colchicine, that is, a dose of 0 mg of colchicine.

In these and other embodiments, the colchicine-responsive condition is gout (e.g., a gout flare in a chronic gout sufferer), familial Mediterranean fever (FMF), thrombocytopenic purpura, pericarditis, scleroderma, or Behçet's disease. In some embodiments, the treatment with colchicine is either palliative or prophylactic. The gout may be acute gout, e.g. a gout flare, or chronic gout.

Acute Gout

Acute gout, or gout flares, can be treated according to the following treatment schedule. This table indicates the original, or intended, dose, i.e., the dose of colchicine recommended absent concomitant administration of the drugs listed below. This table also presents the dose adjustment of the present invention, or the recommended colchicine dose to be administered when the strong and moderate CYP3A4 and P-gp inhibitors are administered concomitantly with colchicine when the patient is being treated for acute gout, or an acute gout flare.

| | Colchicine Dose Recommendation | |
|---|---|---|
| Drug | Original Intended Dose (Total Dose) | Dose Adjustment |
| Strong CYP3A4 Inhibitors | Regimen Reduced by Two Thirds | |
| Erythromycin Ketoconazole Ritonavir | 1.2 mg (2 tablets) at the first sign of the flare followed by 0.6 mg (1 tablet) one hour later. Dose to be repeated no earlier than 3 days. | 0.6 mg (1 tablet) × 1 dose. Dose to be repeated no earlier than 3 days. |
| Moderate CYP3A4 Inhibitors | Regimen Reduced by One Third | |
| Diltiazem Verapamil | 1.2 mg (2 tablets) at the first sign of the flare followed by 0.6 mg (1 tablet) one hour later. Dose to be repeated no earlier than 3 days. | 1.2 mg (2 tablets) × 1 dose. Dose to be repeated no earlier than 3 days. |
| Strong P-gp Inhibitors | Regimen Reduced by Two Thirds | |
| Cyclosporine | 1.2 mg (2 tablets) at the first sign of the flare followed by 0.6 mg (1 tablet) one hour later. Dose to be repeated no earlier than 3 days. | 0.6 mg (1 tablet) × 1 dose. Dose to be repeated no earlier than 3 days. |

Chronic Gout

For chronic gout, an original intended daily dosage amount is 1.2 mg or 6 mg. Alternatively, an intended daily dosage amount of chronic gout can be as much as 2.4 mg per day. The daily dosage amount for chronic gout can be administered at one time or dosed at intervals throughout the day, e.g. twice daily, three times daily, or four times daily.

Chronic gout, with and without a concomitant dose of another drug, can be treated according to the following treatment schedule:

| Colchicine Dose Adjustment for Co-administration with Interacting Drugs If No Alternative Available | | |
|---|---|---|
| | Colchicine Dose Recommendation | |
| Drug | Original Intended Dose | Dose Adjustment |
| Clarithromycin | 0.6 mg twice daily | 0.3 mg once daily |
| | 0.6 mg once daily | 0.3 mg once every other day |
| Cyclosporine | 0.6 mg twice daily | 0.3 mg once daily |
| | 0.6 mg once daily | 0.3 mg once every other day |
| Erythromycin | 0.6 mg twice daily | 0.3 mg once daily |
| | 0.6 mg once daily | 0.3 mg once every other day |
| Ritonavir | 0.6 mg twice daily | 0.6 mg once daily |
| | 0.6 mg once daily | 0.3 mg once daily |

Familial Mediterranean Fever

Familial Mediterranean Fever (FMF) can be treated according to the following intended daily dosing schedule:

| | Daily dosage amount | |
|---|---|---|
| Age | Usual | Maximum |
| Adults and children > 12 years | 1.2 mg | 2.4 mg |
| Children > 6 to 12 years | 0.9 mg | 1.8 mg |
| Children 4 to 6 years | 0.3 mg | 1.8 mg |

When colchicine is given to patients with FMF concomitantly with other drugs, the adjusted (reduced) dosage amount of colchicine, according to this embodiment, is provided in the table below:

| Concomitant Drug Class or Food | Noted or Anticipated Outcome | Clinical Comment |
| --- | --- | --- |
| Strong CYP3A4 Inhibitors: atazanavir, clarithromycin, indinavir, itraconazole, ketoconazole, nefazodone, nelfinavir, ritonavir, saquinavir, telithromycin | Significant increase in colchicine plasma levels[1]; fatal colchicine toxicity has been reported with clarithromycin, a strong CYP3A4 inhibitor. Similarly, significant increase in colchicine plasma levels is anticipated with other strong CYP3A4 inhibitors. | Use colchicine with caution at reduced maximum dose of 0.3 mg twice daily with increased monitoring for adverse effects. In patients with renal or hepatic impairment, use of colchicine in conjunction with these drugs is contraindicated. |
| Moderate CYP3A4 inhibitors: amprenavir, aprepitant, diltiazem, erythromycin, fluconazole, fosamprenavir, grapefruit juice, verapamil | Significant increase in colchicine plasma concentration is anticipated. Neuromuscular toxicity has been reported with diltiazem and verapamil interactions. | Use colchicine with caution at reduced maximum dose of 0.6 mg twice daily with increased monitoring for adverse effects. In patients with renal or hepatic impairment, use a maximum dose of 0.3 mg twice daily. |
| Strong P-gp Inhibitors e.g. Cyclosporine, ranolazine. | Significant increase in colchicine plasma levels[1]; fatal colchicine toxicity has been reported with cyclosporine, a strong P-gp inhibitor. Similarly, significant increase in colchicine plasma levels is anticipated with other strong P-gp inhibitors. | Use colchicine with caution at reduced maximum dose of 0.3 mg twice daily with increased monitoring for adverse effects. In patients with renal or hepatic impairment, use of colchicine in conjunction with these drugs is contraindicated. |

Pharmacy management systems are computer-based systems that are widely used by commercial pharmacies to manage prescriptions and to provide pharmacy and medical personnel with warnings and guidance regarding drugs being administered to individuals. Such systems typically provide alerts warning either or both of health care providers and patients when a drug that may be harmful to the particular patient is prescribed. For example, such systems can provide alerts warning that a patient has an allergy to a prescribed drug, or is receiving concomitant administration of a drug that can have a dangerous interaction with a prescribed drug. U.S. Pat. Nos. 5,758,095, 5,833,599, 5,845,255, 6,014,631, 6,067,524, 6,112,182, 6,317,719, 6,356,873, and 7,072,840, each of which is incorporated herein by reference, disclose various pharmacy management systems and aspects thereof. Many pharmacy management systems are now commercially available, e.g., CENTRICITY Pharmacy from BDM Information Systems Ltd., General Electric Healthcare, Waukesha, Wis., Rx30 Pharmacy Systems from Transaction Data Systems, Inc., Ocoee, Fla., SPEED SCRIPT from Digital Simplistics, Inc., Lenexa, Kans., and various pharmacy management systems from OPUS-ISM, Hauppauge, N.Y.

In another aspect, herein disclosed are methods for using colchicine which methods involve the use of pharmacy management systems.

In one aspect, one such method comprises a pharmacy receiving a prescription for colchicine for a patient who is suffering from gout (e.g., acute gout flares or chronic gout) and who is concomitantly being treated with a second active agent (e.g., ketoconazole or ritonavir) that is an inhibitor of CYP3A and P-glycoprotein, followed by the pharmacy dispensing colchicine in response to receipt of the prescription, wherein the dispensing is preceded by entry into a first computer readable storage medium, in functional communication with a computer, of a unique patient identifier for said patient and at least one drug identifier for colchicine linked to the patient identifier so as to indicate that colchicine is to be administered to the patient. The computer is programmed to issue a drug-drug interaction alert when the at least one drug identifier for colchicine is entered linked to the patient identifier so as to indicate that colchicine is to be administered to the patient and when the patient identifier is also linked to an identifier indicating that a second active agent (e.g., ketoconazole or ritonavir) that is an inhibitor of CYP3A4 or P-glycoprotein is being concomitantly administered to the patient. Upon entry of the at least one drug identifier for colchicine linked to the patient identifier, a drug-drug interaction alert is issued to one or more of a pharmacy technician, a pharmacist, or a pharmacy customer obtaining the colchicine, said alert indicating that a second active agent (e.g., ketoconazole or ritonavir) is being concomitantly administered to the patient and that prior to the colchicine being dispensed, the colchicine dosing regimen must be reviewed and, if necessary adjusted, so that when the colchicine is delivered to the pharmacy customer obtaining the colchicine it is delivered along with instructions for the colchicine to be taken in accordance with a dosing regimen of no more than one about 0.6 mg colchicine dose to start (e.g., following the onset of the acute gout attack or the first sign of a gout flare) followed by either: no additional colchicine doses within about 12, 24, 48, or 72 hours, or at least one additional colchicine dose within about 12 hours and no more frequently than once every hour and wherein each additional colchicine dose is no greater than about 0.6 mg, and wherein the patient ingests the colchicine as instructed.

The drug-drug interaction alert is preferably issued as one or both of a written warning on a display screen of the pharmacy management computer system, and a printed warning. The printed warning may be attached to or packaged with the dispensed prescription.

In one aspect, the identifier indicating that ketoconazole is being concomitantly administered to the patient is an identifier indicating that the second active agent is ketoconazole and is linked to at least one further identifier indicating that the ketoconazole is prescribed so that 200 mg of ketoconazole is to be ingested by the patient daily, in which case the dosing regimen for colchicine is preferably one about 0.6 mg colchicine dose to start, optionally followed by additional colchicine doses, e.g., 0, 1, 2, 3, or 4 additional colchicine doses within 24 hours of about 0.3 mg ingested every 1, 2, 3, 4, 5, 6, 7, 8, 9 10, 11, or 12 hours (e.g., every 2, 3, 4, 5, or 6 hours) after the preceding colchicine dose. In another embodiment, the identifier indicating that ketoconazole is being concomitantly administered to the patient is an identifier indicating that the second active agent is ketoconazole is linked to at least one further identifier, entered into a second computer readable storage medium in functional communication with a computer, the second storage medium being the same as or different from the first storage medium, and the further identifier indicating that the ketoconazole is prescribed so that about 200 mg of ketoconazole is to be ingested by the patient daily, in which case the colchicine dosing regimen is one about 0.6 mg colchicine dose to start, followed by an about 0.3 mg colchicine dose ingested every 1, 2, 3, 4, 5, 6, 7, 8, 9, 10, 11, or 12 hours (e.g., every six to eight hours) after the preceding colchicine dose. In one embodiment, the dosing regimen calls for the about 0.3 mg colchicine dose every six to eight hours. In another embodiment, the dosing regimen calls for one dose of the colchicine every eight to twelve hours.

In yet another preferred aspect, the identifier indicating that ketoconazole is being concomitantly administered to the patient is an identifier indicating that the second active agent is ketoconazole and is linked to at least one further identifier, entered into a second computer readable storage medium in functional communication with a computer, the second storage medium being the same as or different from the first storage medium, and the further identifier indicating that the ketoconazole is prescribed so that about 200 mg of ketoconazole is to be ingested by the patient daily and the dosing regimen is one about 0.3 mg colchicine dose to start, followed by an about 0.3 mg colchicine dose ingested every 2, 3, 4, 5, 6, 7, or 8 hours (e.g., every eight to twelve hours) after the preceding colchicine dose.

A preferred dosing regimen calls for ingestion of colchicine to be continued until a total of no more than 1.2 mg or 2.4 mg of colchicine has been ingested, after which ingestion of colchicine is to be stopped, e.g., for at least 2, 3, 4, 5, 6, or 7 days, or until a subsequent acute gout flare, or the first sign of a subsequent gout flare, occurs.

In another aspect, the identifier indicating that ritonavir is being concomitantly administered to the patient is an identifier indicating that the second active agent is ritonavir and is linked to at least one further identifier indicating that the ritonavir is prescribed so that 200 or 1200 mg of ritonavir is to be ingested by the patient daily, in which case the dosing regimen for colchicine is preferably one about 0.6 mg colchicine dose to start, optionally followed by additional colchicine doses, e.g., 0, 1, 2, 3, or 4 additional colchicine doses within 24 hours of about 0.3 mg ingested every 1, 2, 3, 4, 5, 6, 7, 8, 9 10, 11, or 12 hours (e.g., every 2, 3, 4, 5, or 6 hours) after the preceding colchicine dose. In another embodiment, the identifier indicating that ritonavir is being concomitantly administered to the patient is an identifier indicating that the second active agent is ritonavir is linked to at least one further identifier, entered into a second computer readable storage medium in functional communication with a computer, the second storage medium being the same as or different from the first storage medium, and the further identifier indicating that the ritonavir is prescribed so that about 1200 mg of ritonavir is to be ingested by the patient daily, in which case the colchicine dosing regimen is one about 0.6 mg colchicine dose to start, followed by an about 0.3 mg colchicine dose ingested every 1, 2, 3, 4, 5, 6, 7, 8, 9, 10, 11, or 12 hours (e.g., every six to eight hours) after the preceding colchicine dose. In one embodiment, the dosing regimen calls for the about 0.3 mg colchicine dose every six to eight hours. In another embodiment, the dosing regimen calls for one dose of the colchicine every eight to twelve hours.

In yet another aspect, the identifier indicating that ritonavir is being concomitantly administered to the patient is an identifier indicating that the second active agent is ritonavir and is linked to at least one further identifier, entered into a second computer readable storage medium in functional communication with a computer, the second storage medium being the same as or different from the first storage medium, and the further identifier indicating that the ritonavir is prescribed so that about 1200 mg of ritonavir is to be ingested by the patient daily and the dosing regimen is one about 0.3 mg colchicine dose to start, followed by an about 0.3 mg colchicine dose ingested every 2, 3, 4, 5, 6, 7, or 8 hours (e.g., every eight to twelve hours) after the preceding colchicine dose.

Also disclosed herein is a dosage adjustment method for administering colchicine to a patient to treat a medical condition, the patient concomitantly treated with a second active agent. The second active agent may be, for example, ritonavir, ketoconazole, cyclosporine, verapamil, or diltiazem. The method comprises determining a first colchicine dosing regimen (the colchicine dosing regimen suitable for administration in the absence of co-administration with a second active agent, which dosing regimen may consist of one or more doses of colchicine); and determining a second active agent dosing regimen; and administering the second active agent to the patient at the second active agent dosing regimen while concomitantly administering colchicine to the patient according to a second colchicine dosing regimen, which may consist of one or more reduced colchicine doses. The second colchicine dosing regimen is a fraction of the first colchicine dosing regimen, where the fraction is obtained by administering reduced colchicine doses or by reducing the frequency of colchicine doses, and wherein the fraction is less than or equal to about ⅔ or less than or equal to about ½ or less than or equal to about ⅓.

According to this embodiment, upon the administering the second active agent to the patient at the second active agent dosing regimen while concomitantly administering colchicine to the patient at the second colchicine dosing regimen, the therapeutic circulating level of colchicine is achieved in the patient. Preferably, the fraction is selected from 1/12, ⅙, ¼, ⅓, 5/12, and ½, more preferably, the fraction is ⅓ or ½. In one embodiment, if the second colchicine dosing regimen comprises a "first" colchicine dose, and one or more "subsequent" colchicine doses, each subsequent colchicine dose may be the same as the first dose, or a fraction of the first dose. The fraction is selected from about 1/12, about ⅙, about ¼, about ⅓, about 5/12, about ½, and about 7/12, e.g., about ½ or about ⅔. In one example, the second colchicine dosing regimen is once-a-day, twice-a-day, three-times-a-day or four-times-a-day. In a variation of this example, the initial treatment day in, a second colchicine dosing regimen that lasts for more than one day, has one more dose administered than are administered each subsequent day.

Preferably the second active agent is selected from ketoconazole, cyclosporine, ritonavir, verapamil, or diltiazem. The specific conditions are selected from gout, FMF, thrombocytopenic purpura, and Behçet's disease. In one embodiment, the gout is an acute gout flare and the colchicine treatment schedule is an acute treatment schedule adapted for treatment of acute gout flares, or the gout is chronic gout, and the colchicine treatment schedule is a chronic treatment schedule adapted for prophylaxis, or prevention, of flares. In another embodiment, the fraction of colchicine administered to the patient concomitantly with a second active agent that is a CYP3A4 or P-gp inhibitor is ⅓ or ½ the original intended amount of colchicine and treatment with colchicine is initiated subsequent to or at the same time as initiation of treatment with the second active agent.

Colchicine is one of the most widely used drugs for treating familial Mediterranean fever (FMF). It has been reported that 5-10% of FMF patients do not show a beneficial response to colchicine administration. A polymorphism in the ABCB1 gene, the "ABCB1 3435 C to T polymorphism" has been reported to correlate with this lack of response to colchicine treatment, with patients with the homozygous TT genotype exhibiting the most pronounced "non-responder" phenotypes.

Accordingly, in another aspect, provided herein is a method for treating a patient suffering from FMF, which patient is a colchicine non-responder. Preferably, the patient is homozygous for the TT genotype of the ABCB1 3435 C to T polymorphism. The method entails the concomitant administration of a P-gp inhibitor and colchicine to the patient. Exemplary P-gp inhibitors include ketoconazole and ritonavir. Preferred dosages of the P-gp inhibitor for this purpose correspond to those called for in the prescribing information for the drug in question. For ketoconazole, an exemplary dosage is 200 mg per day. For ritonavir, an exemplary dosage is 200 or 1200 mg per day. Specific colchicine dosing regimens for this purpose are the same as used for treatment of FMF in responders, though the doses of colchicine administered may be increased as tolerated, e.g., up to two to three times the typical doses.

The following examples further illustrate aspects of this disclosure but should not be construed as in any way limiting its scope. In particular, the conditions are merely exemplary and can be readily varied by one of ordinary skill in the art.

EXAMPLES

Example 1

Pharmacokinetic Study in Healthy Adults of Single vs. Multiple Oral Doses of Colchicine Tablets This study was a single-center, open-label, single-sequence, two-period study to evaluate the pharmacokinetic profile of colchicine following single and multiple oral doses of colchicine tablets, 0.6 mg, in healthy volunteers.

In Period 1, study subjects received a 0.6-mg dose of colchicine after an overnight fast of at least 10 hours. In Period 2, subjects received a 0.6 mg dose of colchicine in the morning and the evening (approximately 12 hours later) for 10 days (steady state regimen). Subjects received a light breakfast served 60 minutes following dose administration in the morning and the evening dose was administered 90 minutes after an evening meal on Days 15 through 24 only. On Day 25, the colchicine dose was administered after an overnight fast of at least 10 hours and lunch was served 4 hours post-dose. Study periods were separated by a 14-day washout. Following the single dose and the last dose of the multiple dose regimen (beginning on the mornings of Day 1 and Day 25, respectively), blood samples were collected (6 mL each) from each subject within 1 hour prior to dosing and after dose administration at study hours 0.5, 1, 1.5, 2, 3, 4, 6, 8, 10, 12, and 24 (while confined) and 36, 48, 72, and 96 (on an outpatient basis). Plasma concentrations of colchicine and its metabolites were determined using validated LC/MS-MS methods.

Thirteen healthy, non-smoking subjects with a mean age of 25.5 years (range 19 to 38 years) and within 15% of ideal body weight were enrolled in this study. All subjects completed both dosing periods according to protocol.

After a single dose, plasma concentrations are no longer quantifiable 24 hours post-dose in all but 1 subject. After the last dose of the steady state regimen, concentrations remained quantifiable for 48 to 72 hours. Review of individual subject data shows that no subject experienced a secondary colchicine peak, either following a single dose or upon multiple dosing.

All 2-O-demethylcolchicine (2-DMC) concentrations were below the level of quantitation (LOQ, 0.2 ng/mL) and only one sample from 1 subject (of 13 subjects) had a detectable 3-O-demethylcolchiine (3-DMC) concentration, which was near the level of quantitation. Therefore, metabolites are not discussed further.

In healthy adults, colchicine appears to be readily absorbed when given orally, reaching a mean maximum plasma concentration of 2.5 ng/mL in 1.5 hours after a single dose. The drug is distributed widely, with an apparent volume of distribution of 540 L, greatly exceeding total body water. The elimination half-life as calculated following a single oral dose is approximately 5 hours. Levels were not detectable by 24 hours post-dose and this is therefore not an accurate estimate. Pharmacokinetic parameter values are summarized in the table below.

Review of trough plasma concentrations indicates that steady state was attained by approximately the eighth day of dosing for most subjects. Colchicine may have a diurnal variation reflected in the observed Cmin concentrations at steady state. Cmin concentrations prior to the morning dose are approximately 12% higher than the Cmin concentrations prior to the evening dose (Day 23 and Day 24). The mean Cmin concentration observed on Day 25 was 0.907 ng/mL.

Colchicine accumulated following administration of multiple doses to an extent greater than expected. Exposure was nearly two-fold higher (approximately 1.7 based on AUC [Day 25 $AUC_{0-\tau}$/Day 1 $AUC_{0-\infty}$] and approximately 1.5 based on Cmax [Day 25 $C_{max}$/Day 1 $C_{max}$]). This observation could be attributable to an underestimation of AUC∞ following a single dose. With the higher plasma levels that occur with repeated dosing, a longer terminal elimination half life is apparent, 26.6 hours. Pharmacokinetic parameter values are summarized in Tables 3-5.

TABLE 3

Colchicine Pharmacokinetic Parameter Values Following Administration of
A Single Oral Dose of Colchicine 0.6 mg in Healthy Adults (N = 13)

|  | MEAN | STDEV | % CV | MEDIAN | MIN | MAX |
|---|---|---|---|---|---|---|
| $AUC_{0-t}$ (pg-hr/mL) | 10494.66 | 3544.08 | 33.77 | 10560.90 | 4812.88 | 18091.85 |
| $AUC_{0-inf}$ (pg-hr/mL) | 12268.18 | 4422.08 | 36.05 | 11451.45 | 7252.66 | 23801.68 |
| Cmax (pg/mL) | 2450.15 | 702.11 | 28.66 | 2480.00 | 1584.00 | 3977.00 |
| Tmax (hr) | 1.50 | 0.54 | 36.00 | 1.50 | 1.00 | 3.00 |
| $K_{el}$ (1/hr) | 0.1829 | 0.0592 | 32.38 | 0.1992 | 0.0359 | 0.2443 |
| $T_{1/2}$ (hr) | 4.95 | 4.43 | 89.54 | 3.48 | 2.84 | 19.29 |

TABLE 4

Colchicine Pharmacokinetic Parameter Values Following Administration of
Multiple (b.i.d.) Oral Doses of Colchicine 0.6 mg in Healthy Adults (N = 13)

|  | MEAN | STDEV | % CV | MEDIAN | MIN | MAX |
|---|---|---|---|---|---|---|
| $AUC_{0-t}$ (pg-hr/mL) | 43576.96 | 9333.26 | 21.42 | 41925.10 | 29328.78 | 58265.35 |
| $AUC_{0-\tau}$ (pg-hr/mL) | 20366.61 | 3322.12 | 16.31 | 20423.08 | 13719.18 | 25495.25 |
| $AUC_{0-inf}$ (pg-hr/mL) | 54198.77 | 9214.54 | 17.00 | 54113.43 | 37599.76 | 67944.65 |
| $C_{max}$ (pg/mL) | 3553.15 | 843.45 | 23.74 | 3734.00 | 1977.00 | 4957.00 |
| $C_{min}$ (pg/mL) | 906.51 | 152.19 | 16.79 | 903.50 | 636.23 | 1149.67 |
| $C_{ave}$ (pg/mL) | 1697.22 | 276.84 | 16.31 | 1701.92 | 1143.26 | 2124.60 |
| $T_{max}$ (hr) | 1.31 | 0.60 | 45.61 | 1.00 | 0.50 | 3.00 |
| $K_{el}$ (1/hr) | 0.0267 | 0.0044 | 16.34 | 0.0261 | 0.0206 | 0.0333 |
| $T_{1/2}$ (hr) | 26.60 | 4.33 | 16.26 | 26.51 | 20.82 | 33.65 |

TABLE 5

Mean (% CV) Colchicine Pharmacokinetic Parameter Values
Following Administration of Single and Multiple (b.i.d.)
Oral Doses of Colchicine 0.6 mg in Healthy Adults

|  | Vd/F (L) | CL/F (L/hr) |
|---|---|---|
| Colchicine 0.6-mg Single Dose (N = 13) | | |
| Day 1 | 341 (54.4) | 54.1 (31.0) |
| Colchicine 0.6 mg b.i.d. × 10 days | | |
| Day 25 | 1150 (18.73) | 30.3 (19.0) |

CL = Dose/$AUC_{0-t}$ (Calculated from mean values)

Vd = CL/Ke (Calculated from mean values)

In tables, the parameter CL/F denotes the apparent total body clearance after administration, calculated as Total Dose/Total $AUC0-_{tau}$; and $V_d$/F denotes the apparent total volume of distribution after administration, calculated as Total Dose/(Total $AUC_\infty \times K_{el}$). FIG. 1 shows mean colchicine plasma concentrations following administration of single and multiple oral doses of colchicine 0.6 mg in healthy adults.

Example 2

Clinical Drug-Drug Interaction Study of Colchicine and Clarithromycin

A single-center, open-label, one sequence, two-period study was carried out in 23 healthy subjects. On Day 1, a single 0.6-mg dose of colchicine was administered. After completing a 21-day washout period, all subjects received 250 mg of clarithromycin administered twice daily for 7 days (Days 22 through 29), a sufficient dose and duration to inhibit CYP3A4 and Pgp. On the final day (Day 29), a single dose of colchicine was co-administered with the clarithromycin dose. When combined with steady-state clarithromycin, there is a significant increase in exposure to colchicine as compared to when colchicine is given alone: the mean $C_{max}$ and $AUC_{0-t}$ concentrations increased 167% and 250%, respectively. In addition, co-administration of clarithromycin and colchicine resulted in an increase of 233% in the plasma elimination half-life (t½) of colchicine and a 75% decrease in apparent clearance (CL/F). A summary of the mean (% CV) colchicine pharmacokinetic parameters for Day 1 (colchicine administered alone) and Day 29 (colchicine co-administered with steady-state clarithromycin) are given in the table below and illustrated in Table 5.

TABLE 6

Comparison of Single-Dose Colchicine (0.6 mg, Alone)
and Single-Dose Colchicine (0.6 mg) Co-Administered
with Steady-State Clarithromycin in Healthy Adults

| | Arithmetic Mean (% CV) | |
|---|---|---|
| Parameter (units) | Colchicine (N = 23) | Colchicine + Clarithromycin (N = 23) |
| $AUC_{0-t}$ (ng · hr/mL) | 12.37 (37.64) | 41.95 (23.31) |
| $AUC_{0-inf}$ (ng · hr/mL) | 15.53 (49.6) | 52.62 (22.84) |
| $C_{max}$ (ng/mL) | 2.84 (30.97) | 8.44 (17.63) |
| $T_{max}$ (hr)* | 1.50 (0.50-2.00) | 1.00 (0.50-2.00) |
| CL/F (L/hr) | 46.8 (43.68) | 12.0 (23.75) |

Figure 2:
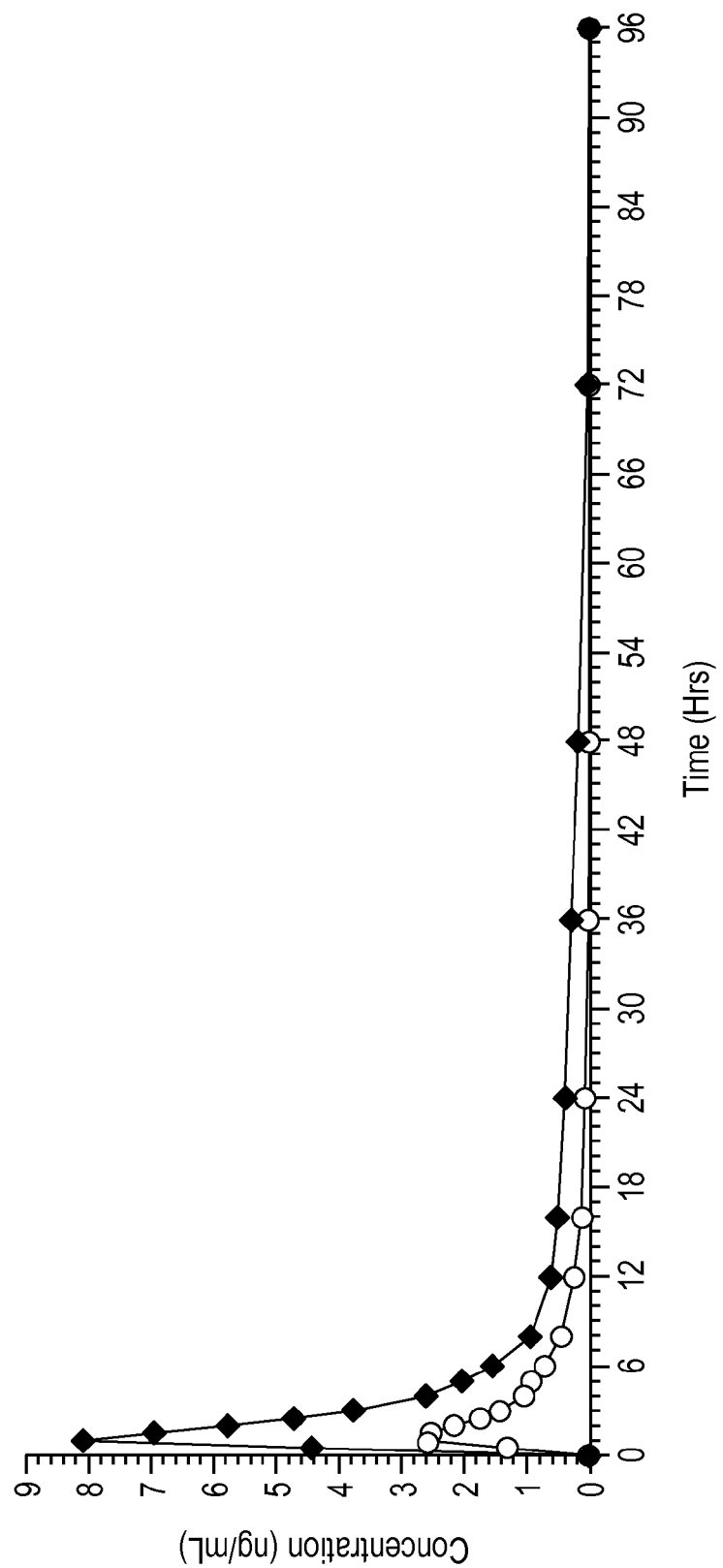
FIG. 2 shows a pharmacokinetic profile comparison of single-dose colchicine (0.6 mg, alone) and single-dose colchicine (0.6 mg) co-administered with steady-state clarithromycin in healthy adults, Y axis=colchicine concentration, ng/mL, X axis=time in hours, N=23, •=colchicine alone, ♦=colchicine plus clarithromycin. See Example 2.

FIG. 2 shows a pharmacokinetic profile comparison of single-dose colchicine (0.6 mg, alone) and single-dose colchicine (0.6 mg) co-administered with steady-state clarithromycin in healthy adults. Based on the foregoing data, it is concluded that the dose of colchicine co-administered with clarithromycin should be reduced by ⅔.

Example 3

Clinical Drug-Drug Interaction Study of Colchicine and Cyclosporine

This study was an open-label, non-randomized, single-center, one-sequence, two-period drug interaction study conducted in healthy male and female volunteers. Twenty-four (24) non-smoking, non-obese adult volunteers were enrolled. All subjects were dosed and studied as a single cohort, with each subject receiving the same treatment in a non-randomized fashion.

A single dose of colchicine, 0.6 mg, was administered alone on Day 1, and then co-administered with cyclosporine on Day 15. Cyclosporine was administered as a single-dose (1×100 mg capsule) on the morning of Day 15. A 14 day washout period was completed after the first colchicine dose on Day 1 and prior to the co-administration of colchicine and cyclosporine doses on Day 15.

Serial blood samples were collected by individual venipuncture up to 96 hours following drug administration on Day 1 and Day 15. Blood samples for determination of colchicine plasma concentrations were obtained at time zero (pre-dose) and after dose administration at 0.5, 1.0, 1.5, 2, 3, 4, 5, 6, 8, 12, and 24 hours post-dose on a confined basis. Subjects were then return to the clinic on a non-confined basis for continued blood sampling collection at 36, 48, 72, and 96 hours post-dose administration on Days 2-5 (Period 1) and Days 16-19 (Period 2). Cyclosporine plasma concentrations were not measured.

TABLE 7

Comparison of Single-Dose Colchicine (0.6 mg, Alone)
and Single-Dose Colchicine (0.6 mg) Co-Administered
with Steady-State Cyclosporine in Healthy Adults

| | Arithmetic Mean (% CV) | |
|---|---|---|
| Parameter (units) | Colchicine (N = 23) | Colchicine + Cyclosporine (N = 23) |
| $AUC_{0-t}$ (ng · hr/mL) | 12.55 | 39.83 |
| $AUC_{0-inf}$ (ng · hr/mL) | 15.00 | 47.31 |
| $C_{max}$ (ng/mL) | 2.72 | 8.82 |
| $T_{max}$ (hr)* | 1.15 | 1.13 |
| CL/F (L/hr) | 48.24 | 13.42 |

Figure 3:
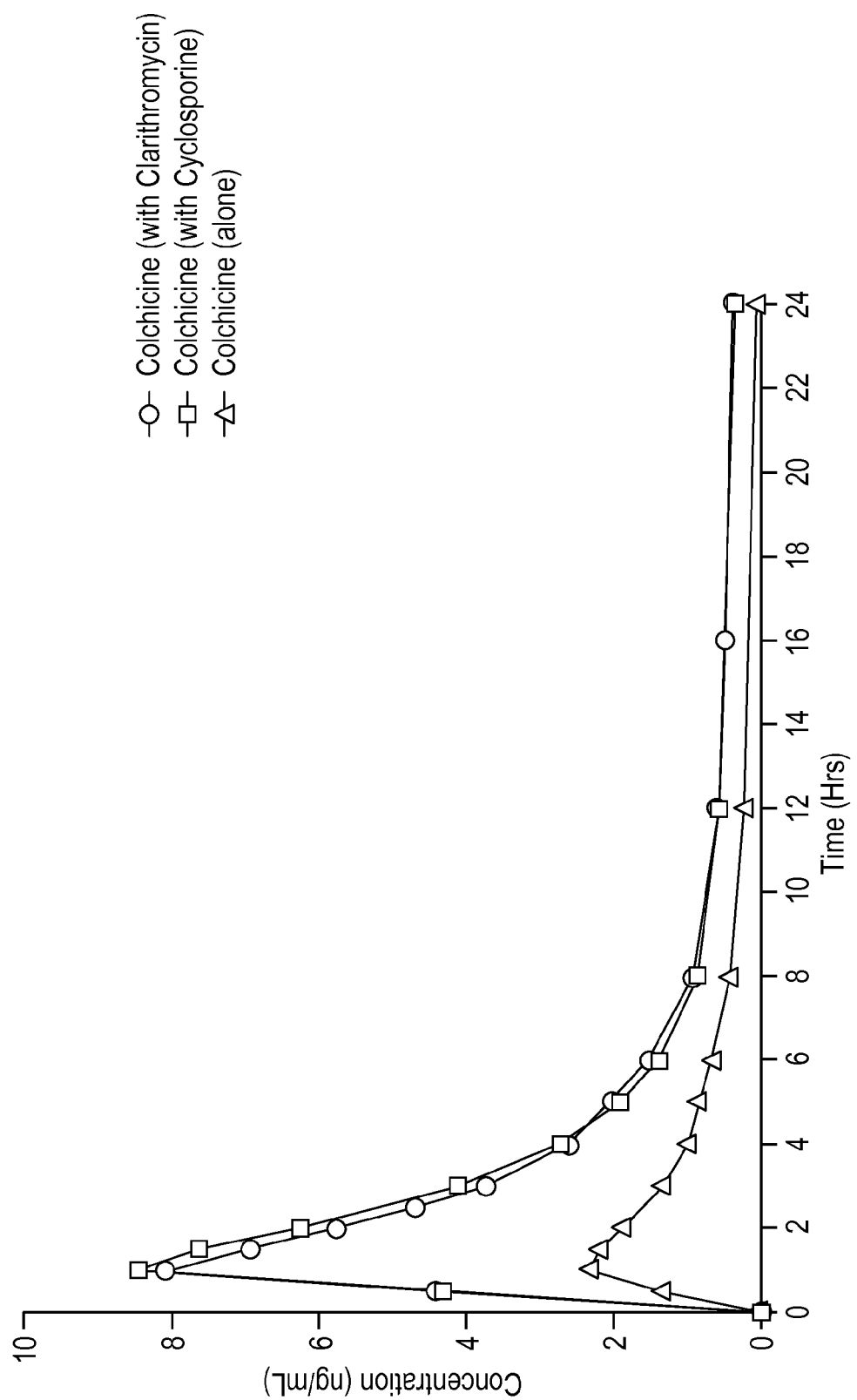
FIG. 3 shows a pharmacokinetic profile comparison of single-dose colchicine (0.6 mg, alone) and single-dose colchicine (0.6 mg) co-administered with steady-state clarithromycin and steady-state cyclosporine in healthy adults. Y axis=colchicine concentration, ng/mL, X axis=time in hours, N=18, ▲=colchicine alone, •=colchicine plus clarithromycin, ■=colchicine plus cyclosporine.

FIG. 3 shows a pharmacokinetic profile comparison of single-dose colchicine (0.6 mg, alone) and single-dose colchicine (0.6 mg) co-administered with steady-state clarithromycin and steady-state cyclosporine in healthy adults. Based on the foregoing data, the dose of colchicine co-administered with cyclosporine should be reduced by approximately ½ to ¾.

Example 4

Clinical Drug-Drug Interaction Study of Colchicine and Ritonavir

An open-label, non-randomized, single-center, one-sequence, two-period drug interaction study was conducted in healthy male and female volunteers; there will be a 14-day washout between the two periods. Twenty-four (24) non-smoking, non-obese adult volunteers were enrolled. All subjects were dosed and studied as a single cohort, with each subject receiving the same treatment in a non-randomized fashion.

All subjects received a single 0.6-mg dose of colchicine on Day 1 administered under standard fasting conditions, followed by a 14-day washout period completed on an outpatient basis. At discharge on Day 2, study subjects were instructed to return to the clinical site on the mornings and evenings of Days 15 through 18 to receive two daily dosage amounts of ritonavir (1×100 mg ritonavir capsule twice daily (every 12 hours) on Days 15-18) in a 'directly-observed' fashion; after taking the first dose of ritonavir, subjects remained in the clinic for observation for 1 hour post-dose administration on Day 15. On the evening of Day 18, study participants remained at the clinic for their final study confinement period. In the morning on Day 19, study subjects received a single 0.6 mg colchicine dose with a single 100 mg ritonavir dose and study subjects received the final 100 mg ritonavir dose 12 hours later in the evening on Day 19 under standard fasting conditions.

Serial blood samples were collected by individual venipuncture up to 96 hours following drug administration on Day 1 and Day 19. Blood samples for determination of colchicine plasma concentrations were obtained at time zero (pre-dose) and after dose administration at 0.5, 1.0, 1.5, 2, 3, 4, 5, 6, 8, 12, and 24 hours post-dose on an inpatient basis. Subjects returned to the clinic on an outpatient basis for continued blood sampling collection at 36, 48, 72, and 96 hours post-dose administration. Ritonavir plasma concentrations were not measured.

TABLE 8

Comparison of Single-Dose Colchicine (0.6 mg, Alone) and Single-Dose Colchicine (0.6 mg) Co-Administered with Steady-State Ritonovir in Healthy Adults: ln-transformed data

|  | Colchicine Alone | Colchicine + Ritonovir | % Ratio |
|---|---|---|---|
| $C_{max}$ (pg/mL), geometric mean | 1798.37 | 4835.39 | 268.88 |
| $AUC_{0-t}$ (pg · h/mL), geometric mean | 7642.71 | 27793.08 | 363.65 |
| $AUC_\infty$ (pg · h/mL), geometric mean | 9551.74 | 33771.36 | 353.56 |

TABLE 9

Comparison of Single-Dose Colchicine (0.6 mg, Alone) and Single-Dose Colchicine (0.6 mg) Co-Administered with Steady-State Ritonavir in Healthy Adults

| | Arithmetic Mean (% CV) Median (Range) for $T_{max}$ | |
|---|---|---|
| Parameter (units) | Colchicine + Ritonavir (N = 18) | Colchicine Alone (N = 18) |
| $AUC_{0-t}$ (ng · hr/mL) | 29.05 (30.76) | 8.41 (47.46) |
| $AUC_{0-\infty}$ (ng · hr/mL) | 35.28 (29.79) | 10.41 (45.48) |
| $C_{max}$ (ng/mL) | 4.99 (25.18) | 1.87 (28.19) |
| $T_{max}$ (hr) | 1.5 (1-1.5) | 1 (0.5-1.5) |
| CL/F (L/hr) | 18.59 (31.58) | 67.93 (39.47) |

Following exposure to 100 mg b.i.d.×5 days, there was a significant increase in exposure to a single 0.6-mg colchicine (approximately 245%). Mean peak colchicine concentration increased by approximately 170%. Total apparent oral clearance was decreased by 70% with co-administration. $T_{max}$ is not affected. Elimination half-life could not be estimated accurately as plasma concentrations were not quantifiable after 24 hours.

Figure 4:
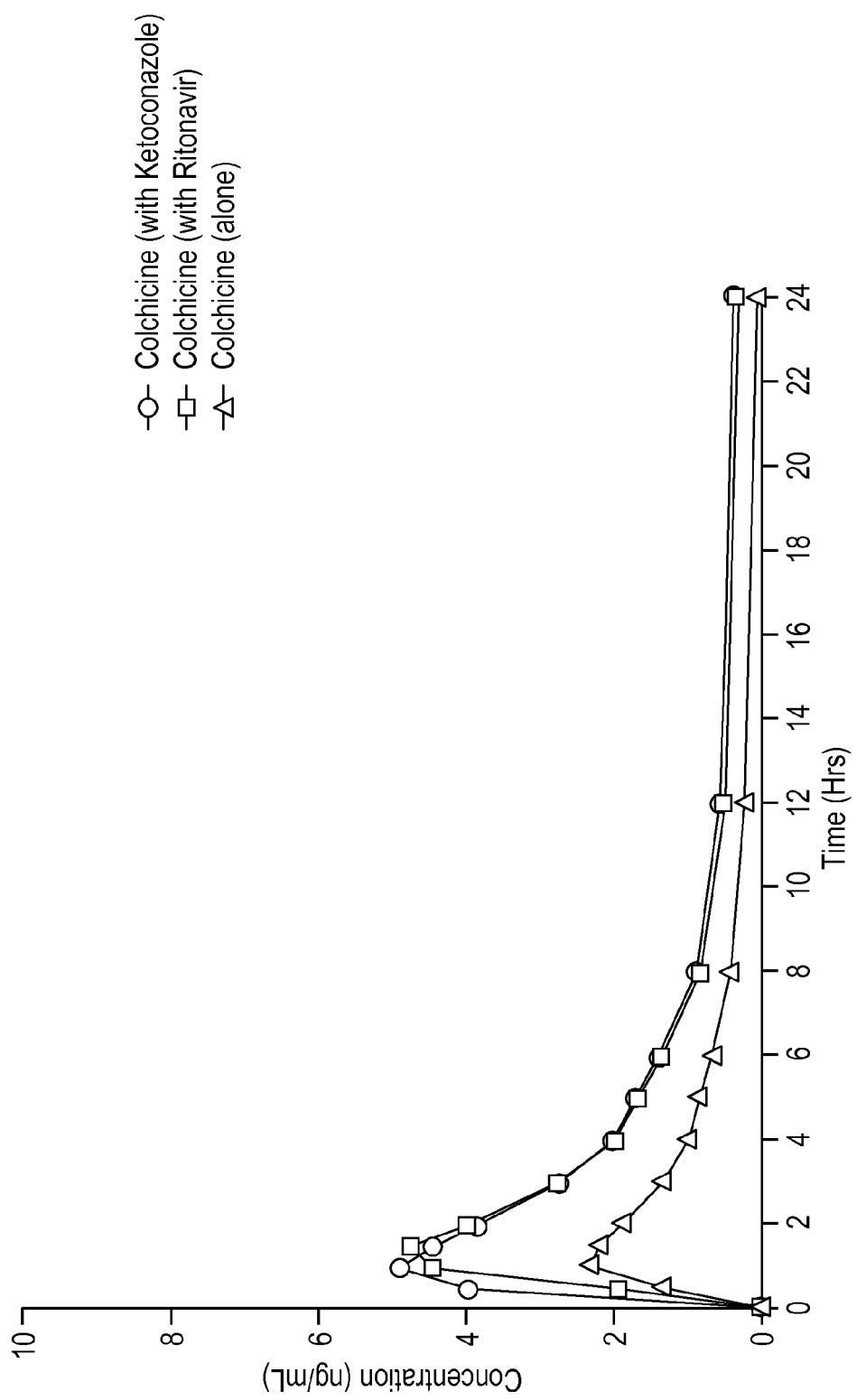
FIG. 4 shows a pharmacokinetic profile comparison of single-dose colchicine (0.6 mg, alone) and single-dose colchicine (0.6 mg) co-administered with steady-state ketoconazole and steady-state ritonavir in healthy adults. Y axis=colchicine concentration, ng/mL, X axis=time in hours, N=18, ▲=colchicine alone, •=colchicine plus ketoconazole, ■=colchicine plus ritonavir.

FIG. 4 shows a pharmacokinetic profile comparison of single-dose colchicine (0.6 mg, alone) and single-dose colchicine (0.6 mg) co-administered with steady-state ritonavir and steady-state ketoconazole in healthy adults. Based on the foregoing data, the dose of colchicine co-administered with ritonavir should be reduced by approximately ½.

Example 5

Clinical Drug-Drug Interaction Study of Colchicine and Ketoconazole

This study was an open-label, non-randomized, single-center, one-sequence, two-period drug interaction study conducted in healthy male and female volunteers; there will be a 14-day washout between the two periods. Twenty-four (24) non-smoking, non-obese adult volunteers were enrolled.

A single dose of colchicine, 0.6 mg, was administered alone on Day 1, and then co-administered with ketoconazole on Day 19 (AM dose). Ketoconazole was administered for 5 consecutive days [200 mg twice daily (every 12 hours)] beginning on the morning of Day 15, with the last 200 mg ketoconazole dose administered on the evening on Day 19. Total study participation, exclusive of up to 28 days of screening, was approximately 24 days, during which subjects will be confined on two occasions for a total confinement of approximately 3 days.

Serial blood samples were collected by individual venipuncture up to 96 hours following drug administration on Day 1 and Day 19. Blood samples for determination of colchicine plasma concentrations were obtained at time zero (pre-dose) and after dose administration at 0.5, 1.0, 1.5, 2, 3, 4, 5, 6, 8, 12, and 24 hours post-dose on an inpatient basis. Subjects then returnee to the clinic on an outpatient basis for continued blood sampling collection at 36, 48, 72, and 96 hours post-dose administration. Ketoconazole plasma concentrations were not measured.

TABLE 10

Comparison of Single-Dose Colchicine (0.6 mg, Alone) and Single-Dose Colchicine (0.6 mg) Co-Administered with Steady-State Ketoconazole in Healthy Adults: ln-transformed data

|  | Colchicine Alone | Colchicine + Ketoconazole | % Ratio |
|---|---|---|---|
| $C_{max}$ (pg/mL), geometric mean | 2598.28 | 5078.50 | 195.46 |
| $AUC_{0-t}$ (pg · h/mL), geometric mean | 11087.99 | 33223.80 | 299.64 |
| $AUC_\infty$ (pg · h/mL), geometric mean | 13185.92 | 42143.00 | 319.61 |

TABLE 11

Comparison of Single-Dose Colchicine (0.6 mg, Alone) and Single-Dose Colchicine (0.6 mg) Co-Administered with Steady-State Ketoconazole in Healthy Adults

| | Arithmetic Mean (% CV) | |
|---|---|---|
| Parameter (units) | Colchicine (N = 23) | Colchicine + Ketoconazole (N = 23) |
| $AUC_{0-t}$ (pg · hr/mL) | 11988.61 | 34382.82 |
| $AUC_{0-inf}$ (pg · hr/mL) | 14314.09 | 43688.90 |
| $C_{max}$ (pg/mL) | 2779.08 | 5266.92 |
| $T_{max}$ (hr)* | 1.00 | 1.02 |
| CL/F (L/hr) | 49301.09 | 14797.94 |

*Median (Range) for $T_{max}$

Following administration of ketoconazole 200 mg b.i.d.×5 days, there was a significant increase in exposure to a single oral dose of colchicine 0.6 mg ($C_{max}$ and $AUC_{0-t}$ increased by 90% and 190%, respectively, and $AUC_{0-\infty}$ increased by about 205%). Total apparent oral clearance decreased by 70% with co-administration. Elimination half-life could not be estimated accurately as plasma concentrations were not quantifiable after 24 hours.

FIG. 4 shows a pharmacokinetic profile comparison of single-dose colchicine (0.6 mg, alone) and single-dose colchicine (0.6 mg) co-administered with steady-state ritonavir and steady-state ketoconazole in healthy adults. Based on the foregoing data, the dose of colchicine co-administered with ketoconazole should be reduced by approximately ½.

Example 6

Clinical Drug-Drug Interaction Study of Colchicine and Azithromycin

This study was an open-label, non-randomized, single-center, one-sequence, two-period drug interaction study conducted in healthy male and female volunteers; there was a 14-day washout between the two periods. Twenty-four (24)

non-smoking, non-obese adult volunteers were enrolled. All subjects were dosed and studied as a single cohort, with each subject receiving the same treatment in a non-randomized fashion.

A single dose of colchicine, 0.6 mg, was administered alone on Day 1, and then co-administered with the azithromycin on Day 19. Azithromycin was administered for 5 consecutive days (2×250 mg once daily [Day 15 only] and then 1×250 mg once daily Days 16-19) beginning on the morning of Day 15, with the last 250 mg azithromycin dose administered on the morning on Day 19. Total study participation, exclusive of up to 28 days of screening, was approximately 24 days, during which subjects were confined on two occasions for a total confinement of approximately 3 days.

Serial blood samples were collected by individual venipuncture up to 96 hours following drug administration on Day 1 and Day 19. Blood samples for determination of colchicine plasma concentrations were obtained at time zero (pre-dose) and after dose administration at 0.5, 1.0, 1.5, 2, 3, 4, 5, 6, 8, 12, and 24 hours post-dose on an inpatient basis. Subjects returned to the clinic on an outpatient basis for continued blood sampling collection at 36, 48, 72, and 96 hours post-dose administration. Azithromycin plasma concentrations were not measured.

TABLE 12

Comparison of Single-Dose Colchicine (0.6 mg, Alone) and Single-Dose Colchicine (0.6 mg) Co-Administered with Steady-State Azithromycin in Healthy Adults

|  | Colchicine Alone | Colchicine + Azithromycin | % Ratio |
| --- | --- | --- | --- |
| $C_{max}$ (pg/mL), geometric mean | 2535.94 | 2856.22 | 112.63 |
| $AUC_{0-t}$ (pg · h/mL), geometric mean | 10971.51 | 16090.52 | 146.66 |
| $AUC_\infty$ (pg · h/mL), geometric mean | 12931.80 | 18312.83 | 141.61 |

TABLE 13

Comparison of Single-Dose Colchicine (0.6 mg, Alone) and Single-Dose Colchicine (0.6 mg) Co-Administered with Steady-State Azithromycin in Healthy Adults

|  | Arithmetic Mean (% CV) Median (Range) for $T_{max}$ | |
| --- | --- | --- |
| Parameter (units) | Colchicine + Azithromycin (N = 21) | Colchicine Alone (N = 21) |
| $AUC_{0-t}$ (ng · hr/mL) | 17.16 (37.78) | 11.98 (45.81) |
| $AUC_{0-\infty}$ (ng · hr/mL) | 19.61 (39.15) | 14.13 (46.73) |
| $C_{max}$ (ng/mL) | 3.05 (39.54) | 2.74 (41.52) |
| $T_{max}$ (hr) | 1.5 (0.5-3) | 1.0 (0.5-3) |
| $t_{1/2}$ (hr) | 6.71 (68.34)[1] | 6.07 (66.15)[1] |
| CL/F (L/hr) | 35.01 (37.26) | 50.24 (40.31) |

Following administration of azithromycin 500 mg on Day 1 followed by 250 mg×4 days, exposure to colchicine is increased (approximately 46% for $AUC_{0-t}$ and approximately 40% for $AUC_{0-\infty}$). Mean peak colchicine concentration increased by approximately 12% and total apparent oral clearance decreased approximately 30% with co-administration. $T_{max}$ was not affected.

FIG. 5 shows a pharmacokinetic profile comparison of single-dose colchicine (0.6 mg, alone) and single-dose colchicine (0.6 mg) co-administered with steady-state azithromycin and steady-state diltiazem in healthy adults.

Example 7

Clinical Drug-Drug Interaction study of Colchicine and Diltiazem

This study was an open-label, non-randomized, single-center, one-sequence, two-period drug interaction study conducted in healthy male and female volunteers. Twenty-four (24) non-smoking, non-obese adult volunteers were enrolled. All subjects were dosed and studied as a single cohort, with each subject receiving the same treatment in a non-randomized fashion.

As single dose of colchicine, 0.6 mg, was administered alone on Day 1, and then co-administered with diltiazem ER on Day 21. Diltiazem ER was administered for 7 consecutive days (1×240 mg capsule once daily on Days 15-21) beginning on the morning of Day 15, with the last 240 mg diltiazem ER dose administered on the morning on Day 21. A 14-day washout period was completed after the first colchicine dose on Day 1 and prior to the administration of the first diltiazem ER dose on Day 15.

Serial blood samples were collected by individual venipuncture up to 96 hours following drug administration on Day 1 and Day 21. Blood samples for determination of colchicine plasma concentrations were obtained at time zero (pre-dose) and after dose administration at 0.5, 1.0, 1.5, 2, 3, 4, 5, 6, 8, 12, and 24 hours post-dose on an inpatient basis. Subjects returned to the clinic on an outpatient basis for continued blood sampling collection at 36, 48, 72, and 96 hours post-dose administration. Diltiazem plasma concentrations were not measured.

TABLE 14

Comparison of Single-Dose Colchicine (0.6 mg, Alone) and Single-Dose Colchicine (0.6 mg) Co-Administered with Steady-State Diltiazem in Healthy Adults

|  | Colchicine Alone | Colchicine + Diltiazem | % Ratio |
| --- | --- | --- | --- |
| $C_{max}$ (pg/mL), geometric mean | 2006.42 | 2583.22 | 128.75 |
| $AUC_{0-t}$ (pg · h/mL), geometric mean | 9154.55 | 15740.37 | 171.94 |
| $AUC_\infty$ (pg · h/mL), geometric mean | 11022.30 | 19902.98 | 180.57 |

TABLE 15

Comparison of Single-Dose Colchicine (0.6 mg, Alone) and Single-Dose Colchicine (0.6 mg) Co-Administered with Steady-State Diltiazem in Healthy Adults

|  | Arithmetic Mean (% CV) Median (Range) for $T_{max}$ | |
| --- | --- | --- |
| Parameter (units) | Colchicine + Diltiazem (N = 20) | Colchicine Alone (N = 20) |
| $AUC_{0-t}$ (ng · hr/mL) | 17.73 | 10.04 |
| $AUC_{0-\infty}$ (ng · hr/mL) | 22.49 | 12.03 |
| $C_{max}$ (ng/mL) | 2.80 | 2.17 |
| $T_{max}$ (hr) | 1.48 | 1.15 |
| $t_{1/2}$ (hr) | 12.50 | 5.51 |
| CL/F (L/hr) | 463.49 | 395.83 |

FIG. 5 shows a pharmacokinetic profile comparison of single-dose colchicine (0.6 mg, alone) and single-dose colchicine (0.6 mg) co-administered with steady-state azithromycin and steady-state diltiazem in healthy adults.

Example 8

Clinical Drug-Drug Interaction Study of Colchicine and Verapamil

This study was an open-label, non-randomized, single-center, one-sequence, two-period drug interaction study conducted in healthy male and female volunteers. Twenty-four (24) non-smoking, non-obese adult volunteers were enrolled. All subjects were dosed and studied as a single cohort, with each subject receiving the same treatment in a non-randomized fashion.

A single dose of colchicine, 0.6 mg, was administered alone on Day 1, and then co-administered with verapamil HCl ER on Day 19. Verapamil HCl ER was administered for 5 consecutive days (1×240 mg tablet once daily on Days 15-19) beginning on the morning of Day 15, with the last 240 mg verapamil HCl ER dose administered on the morning on Day 19. A 14-day washout period was completed after the first colchicine dose on Day 1 and prior to the administration of the first verapamil HCL ER dose on Day 15.

Serial blood samples were collected by individual venipuncture up to 96 hours following drug administration on Day 1 and Day 19. Blood samples for determination of colchicine plasma concentrations were obtained at time zero (pre-dose) and after dose administration at 0.5, 1.0, 1.5, 2, 3, 4, 5, 6, 8, 12, and 24 hours post-dose on a confined basis. Subjects returned to the clinic on a non-confined basis for continued blood sampling collection at 36, 48, 72, and 96 hours post-dose administration on Days 2-5 (Period 1) and Days 20-23 (Period 2). Verapamil plasma concentrations were not measured.

TABLE 16

Comparison of Single-Dose Colchicine (0.6 mg, Alone) and Single-Dose Colchicine (0.6 mg) Co-Administered with Steady-State Verapamil in Healthy Adults

|  | Colchicine Alone | Colchicine + Verapamil | % Ratio |
|---|---|---|---|
| $C_{max}$ (pg/mL), geometric mean | 2768.77 | 3639.68 | 131.45 |
| $AUC_{0-t}$ (pg · h/mL), geometric mean | 12256.40 | 23889.21 | 194.94 |
| $AUC_{\infty}$ (pg · h/mL), geometric mean | 14415.79 | 29556.75 | 205.03 |

TABLE 17

Comparison of Single-Dose Colchicine (0.6 mg, Alone) and Single-Dose Colchicine (0.6 mg) Co-Administered with Steady-State Verapamil in Healthy Adults

| | Arithmetic Mean (% CV) Median (Range) for $T_{max}$ ||
|---|---|---|
| Parameter (units) | Colchicine + Verapamil (N = 24) | Colchicine Alone (N = 24) |
| $AUC_{0-t}$ (ng · hr/mL) | 24.64 | 13.09 |
| $AUC_{0-\infty}$ (ng · hr/mL) | 30.59 | 15.37 |
| $C_{max}$ (ng/mL) | 3.85 | 2.97 |
| $T_{max}$ (hr) | 1.15 | 1.22 |
| $t_{1/2}$ (hr) | 17.17 | 6.24 |
| CL/F (L/hr) | 21.01 | 43.93 |

Recitation of ranges of values herein are merely intended to serve as a shorthand method of referring individually to each separate value falling within the range, unless otherwise indicated herein, and each separate value is incorporated into the specification as if it were individually recited herein. The endpoints of all ranges directed to the same component or property are inclusive and independently combinable.

All methods described herein can be performed in a suitable order unless otherwise indicated or clearly contradicted by context. The use of any and all examples, or exemplary language (e.g., "such as") herein is intended to better illuminate the disclosure and is non-limiting unless otherwise specified. No language in the specification should be construed as indicating that any non-claimed element as essential to the practice of the claimed embodiments. Unless defined otherwise, technical and scientific terms used herein have the same meaning as is commonly understood by one of skill in the art to which this disclosure belongs. The terms wt %, weight percent, percent by weight, etc. are equivalent and interchangeable.

In the specification and claims that follow, references will be made to a number of terms which shall be defined to have the following meaning.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

"Concomitant" and "concomitantly" as used herein refer to the administration of at least two drugs to a patient either simultaneously or within a time period during which the effects of the first administered drug are still operative in the patient. Thus, if the first drug is, e.g., clarithromycin and the second drug is colchicine, the concomitant administration of the second drug can occur as much as one to two weeks, preferably within one to seven days, after the administration of the first drug. This is because clarithromycin can exert a long-lasting inhibition of CYP3A isozymes so that CYP3A activity in the patient may not return to pre-clarithromycin-administration levels for as much as two weeks after the cessation of clarithromycin administration. If colchicine is the first drug, administration of a second drug would be concomitant if done within 1 to 2 days, preferably 12 to 24 hours.

A "dose" means the measured quantity of a drug to be taken at one time by a patient.

A "dosage amount" means an amount of a drug suitable to be taken during a fixed period, usually during one day (i.e. daily). A "daily dosage amount" is the total dosage amount taken in one day, that is, a 24 hour period.

"Dosing regimen" means the dose of a drug taken at a first time by a patient and the interval (time or symptomatic) and dosage amounts at which any subsequent doses of the drug are taken by the patient. Each dose may be of the same or different.

A "patient" means a human or non-human animal in need of medical treatment. Medical treatment can include treatment of an existing condition, such as a disease or disorder, prophylactic or preventative treatment, or diagnostic treatment. In preferred embodiments the patient is human.

"Providing" means giving, administering, selling, distributing, transferring (for profit or not), manufacturing, compounding, or dispensing.

"Risk" means the probability or chance of adverse reaction, injury, or other undesirable outcome arising from a medical treatment. An "acceptable risk" means a measure of the risk of harm, injury, or disease arising from a medical treatment that will be tolerated by an individual or group. Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility.

Pharmacokinetic parameters referred to herein describe the in vivo characteristics of drug (or a metabolite or a surrogate marker for the drug) over time. These include plasma concentration (C), as well as $C_{max}$, $C_n$, $C_{24}$, $T_{max}$, and AUC. "$C_{max}$" is the measured plasma concentration of the active agent at the point of maximum, or peak, concentration. "$C_{min}$" is the measured plasma concentration of the active agent at the point of minimum concentration. "$C_n$" is the measured plasma concentration of the active agent at about n hours after administration. "$C_{24}$" is the measured plasma concentration of the active agent at about 24 hours after administration. The term "$T_{max}$" refers to the time from drug administration until $C_{max}$ is reached. "AUC" is the area under the curve of a graph of the measured plasma concentration of an active agent vs. time, measured from one time point to another time point. For example $AUC_{0-t}$ is the area under the curve of plasma concentration versus time from time 0 to time t, where time 0 is the time of initial administration of the drug. Time t can be the last time point with measurable plasma concentration for an individual formulation. The $AUC_{0-\infty}$, $AUC_{\infty}$ or $AUC_{0-inf}$ is the calculated area under the curve of plasma concentration versus time from time 0 to time infinity. In steady-state studies, $AUC_{0-\tau}$ is the area under the curve of plasma concentration over the dosing interval (i.e., from time 0 to time τ (tau), where tau is the length of the dosing interval. Other pharmacokinetic parameters are the parameter $K_e$ or $K_{el}$, the terminal elimination rate constant calculated from a semi-log plot of the plasma concentration versus time curve; $t_{1/2}$ the terminal elimination half-life, calculated as $0.693/K_{el}$. CL/F denotes the apparent total body clearance after administration, calculated as Total Dose/Total $AUC_{\infty}$; and $V_{area}/F$ denotes the apparent total volume of distribution after administration, calculated as Total Dose/(Total $AUC_{\infty} \times K_{el}$).

"Side effect" means a secondary effect resulting from taking a drug. The secondary effect can be a negative (unfavorable) effect (i.e., an adverse side effect) or a positive (favorable) effect.

The most frequently reported adverse side effects to colchicine therapy are gastrointestinal, specifically abdominal pain with cramps, diarrhea, nausea, and vomiting. Less frequently or rarely reported adverse side effects associated with colchicine therapy include anorexia, agranulocytosis, allergic dermatitis, allergic reactions, alopecia, angioedema, aplastic anemia, bone marrow depression, myopathy, neuropathy, skin rash, thrombocytopenic disorder, and urticaria.

Whether a patient experiences an adverse side effect can be determined by obtaining information from the patient regarding onset of certain symptoms which may be indicative of the adverse side effect, results of diagnostic tests indicative of the adverse side effect, and the like.

Embodiments are described herein, including the best modes known to the inventors. Variations of such embodiments will become apparent to those of ordinary skill in the art upon reading the foregoing description. The skilled artisan is expected to employ such variations as appropriate, and the disclosed methods are expected to be practiced otherwise than as specifically described herein. Accordingly, all modifications and equivalents of the subject matter recited in the claims appended hereto are included to the extent permitted by applicable law. Moreover, any combination of the above-described elements in all possible variations thereof is encompassed unless otherwise indicated herein or otherwise clearly contradicted by context.

What is claimed is:

1. A method of treating a patient in need of treatment for gout or familial Mediterranean fever with colchicine, comprising
    orally administering an adjusted daily dosage amount of colchicine to the patient who is receiving concomitant administration of a recommended daily dosage amount of ritonavir,
    wherein the adjusted daily dosage amount of colchicine is 25% to 50% of a daily dosage amount of colchicine suitable for the patient if the patient were not receiving concomitant ritonavir.

2. The method of claim 1, wherein treating with colchicine is for the prophylaxis of gout flares, and wherein the daily dosage amount of colchicine suitable for the patient if the patient were not receiving concomitant ritonavir is 0.6 mg twice daily or 0.6 mg once daily.

3. The method of claim 2 wherein the adjusted daily dosage amount of colchicine is 0.3 mg once daily.

4. The method of claim 2, wherein the adjusted daily dosage amount of colchicine is 0.3 mg once every other day.

5. The method of claim 1, wherein treating with colchicine is for the treatment of gout flares, and wherein the daily dosage amount of colchicine suitable for the patient if the patient were not receiving concomitant ritonavir is 1.2 mg at the first sign of flare, followed by 0.6 mg one hour later, dose to be repeated no earlier than 3 days.

6. The method of claim 5, wherein the adjusted daily dosage amount is 0.6 mg at the first sign of a flare, followed by 0.3 mg one hour later, dose to be repeated no earlier than 3 days.

7. The method of claim 1, wherein treating with colchicine is for treatment of familial Mediterranean fever, and wherein the adjusted daily dosage amount of colchicine is a maximum colchicine dosage amount of 0.3 mg of colchicine twice daily, which is a reduction from the intended daily dosage amount of colchicine in the absence of concomitant ritonavir wherein the intended daily dosage amount is a maximum daily dosage amount as follows:

|  | Daily dosage amount | |
| --- | --- | --- |
| Age | Usual | Maximum |
| Adults and children > 12 years | 1.2 mg | 2.4 mg |
| Children > 6 to 12 years | 0.9 mg | 1.8 mg |
| Children 4 to 6 years | 0.3 mg | 1.8 mg. |

8. The method of claim 1, wherein the recommended daily dosage amount of ritonavir is 200 mg to 1200 mg per day.

9. The method of claim 1, wherein the recommended daily dosage amount of ritonavir is 200 mg or 1200 mg per day.

* * * * *

UNITED STATES PATENT AND TRADEMARK OFFICE
CERTIFICATE OF CORRECTION

PATENT NO. : 8,093,297 B2  
APPLICATION NO. : 13/092459  
DATED : January 10, 2012  
INVENTOR(S) : Matthew W. Davis Page 1 of 4

It is certified that error appears in the above-identified patent and that said Letters Patent is hereby corrected as shown below:

On page 2, under "OTHER PUBLICATIONS", in column 1, line 8, delete "Colcyrs" and insert -- COLCRYS --, therefor.

On page 2, under "OTHER PUBLICATIONS", in column 2, line 29, delete "Achert" and insert -- Achtert --, therefor.

In column 1, line 1, after "Continuation" insert -- of --.

In column 1, lines 12-13, delete "Dec. 17, 2008" and insert -- January 14, 2009 --, therefor.

In column 2, lines 22-23, delete "3-demethylchochicine" and insert -- 3-demethylcolchicine --, therefor.

In column 3, line 8, delete "in a" and insert -- in an --, therefor.

In column 3, line 51, delete "that that" and insert -- that --, therefor.

In column 4, line 45, delete "●" and insert -- ○ --, therefor.

In column 4, line 52, delete "▲" and insert -- Δ --, therefor.

In column 4, line 52, delete "●" and insert -- ○ --, therefor.

In column 4, line 53, delete "■" and insert -- □ --, therefor.

In column 4, line 59, delete "▲" and insert -- Δ --, therefor.

In column 4, line 59, delete "●" and insert -- ○ --, therefor.

Signed and Sealed this  
Twenty-third Day of October, 2012

David J. Kappos  
*Director of the United States Patent and Trademark Office*

In column 4, line 60, delete "■" and insert -- □ --, therefor.

In column 4, line 66, delete "▲" and insert -- Δ --, therefor.

In column 4, line 66, delete "●" and insert -- ○ --, therefor.

In column 4, line 67, delete "■" and insert -- □ --, therefor.

In column 6, line 52, delete "in a" and insert -- in --, therefor.

In column 8, line 62, after "may" insert -- be --.

In column 8, line 65, delete "wherein the" and insert -- the --, therefor.

In column 9, line 9, after "amount" insert -- is --.

In column 9, line 37, after "may" insert -- be --.

In column 9, line 40, delete "wherein the" and insert -- the --, therefor.

In column 9, line 50, after "amount" insert -- is --.

In column 10, line 12, after "may" insert -- be --.

In column 10, line 15, delete "wherein the" and insert -- the --, therefor.

In column 10, line 26, after "amount" insert -- is --.

In column 10, line 66, after "may" insert -- be --.

In column 11, line 8, after "amount" insert -- is --.

In column 12, line 26, delete "amount of" and insert -- amount for --, therefor.

In column 12, line 37, before "Colchicine" insert -- Table 2 --.

In column 13, line 6, delete "levels[1]" and insert -- levels --, therefor.

In column 13, line 23, delete "levels[1]" and insert -- levels --, therefor.

In column 15, line 11, delete "9" and insert -- 9, --, therefor.

In column 15, line 61, delete "9" and insert -- 9, --, therefor.

In column 16, line 49, delete "the administering" and insert -- administering --, therefor.

In column 18, line 23, delete "are" and insert -- were --, therefor.

In column 18, line 34, delete "3-O-demethylcolchciine" and insert -- 3-O-demethylcolchicine --, therefor.

In column 18, line 52, delete "Cmin" and insert -- $C_{min}$ --, therefor.

In column 18, line 53, delete "Cmin" and insert -- $C_{min}$ --, therefor.

In column 18, line 54, delete "Cmin" and insert -- $C_{min}$ --, therefor.

In column 18, line 56, delete "Cmin" and insert -- $C_{min}$ --, therefor.

In column 18, line 61, delete "Cmax" and insert -- $C_{max}$ --, therefor.

In column 18, line 62, delete "AUC∞" and insert -- $AUC_{\infty}$ --, therefor.

In column 19, line 10, delete "Cmax" and insert -- $C_{max}$ --, therefor.

In column 19, line 12, delete "Tmax" and insert -- $T_{max}$ --, therefor.

In column 19, line 48, delete "Vd/F" and insert -- $V_d/F$ --, therefor.

In column 19, line 59, delete "Vd = CL/Ke" and insert -- $V_d = CL/K_e$ --, therefor.

In column 19, line 63, delete "AUC0-tau;" and insert -- $AUC_{0-tau}$; --, therefor.

In column 20, line 54, delete "Pgp" and insert -- P-gp --, therefor.

In column 20, line 62, delete "(t1/2)" and insert -- $(t_{1/2})$ --, therefor.

In column 20, lines 66-67, after "below" delete "and illustrated in Table 5".

In column 21, line 13, after "$T_{max}$ (hr)" delete "*".

In column 21, lines 48-49, delete "were then return" and insert -- then returned --, therefor.

In column 21, line 61, after "Arithmetic Mean" delete "(% CV)".

In column 22, line 6, after "Arithmetic Mean" delete "(% CV)".

In column 22, line 12, after "$T_{max}$ (hr)" delete "*".

CERTIFICATE OF CORRECTION (continued)
U.S. Pat. No. 8,093,297 B2

In column 22, line 33, delete "will be" and insert -- was --, therefor.

In column 23, line 4, delete "Ritonovir" and insert -- Ritonavir --, therefor.

In column 23, line 7, delete "Ritonovir" and insert -- Ritonavir --, therefor.

In column 23, line 55, delete "will be" and insert -- was --, therefor.

In column 23, lines 65-66, delete "will be" and insert -- were --, therefor.

In column 24, line 7, delete "returnee" and insert -- returned --, therefor.

In column 24, line 32, after "Arithmetic Mean" delete "(% CV)".

In column 24, line 42, after "*Median" delete "(Range)".

In column 25, line 56, delete "(68.34)[1]" and insert -- (68.34) --, therefor.

In column 25, line 56, delete "(66.15)[1]" and insert -- (66.15) --, therefor.

In column 26, line 16, delete "As" and insert -- A --, therefor.

In column 26, line 56, after "Arithmetic Mean" delete "(% CV)".

In column 26, line 57, after "Median" delete "(Range)".

In column 27, line 56, after "Arithmetic Mean" delete "(% CV)".

In column 28, line 57, after "Median" delete "(Range)".